US007779694B2

(12) United States Patent
Iizuka

(10) Patent No.: US 7,779,694 B2
(45) Date of Patent: Aug. 24, 2010

(54) ULTRASONIC TESTING SYSTEM AND ULTRASONIC TESTING TECHNIQUE FOR PIPE MEMBER

(75) Inventor: Yukinori Iizuka, Kanagawa (JP)

(73) Assignee: JFE Steel Corporation, Tokyo (JP)

( * ) Notice: Subject to any disclaimer, the term of this patent is extended or adjusted under 35 U.S.C. 154(b) by 119 days.

(21) Appl. No.: 12/083,321

(22) PCT Filed: Nov. 21, 2006

(86) PCT No.: PCT/JP2006/323636

§ 371 (c)(1),
(2), (4) Date: Apr. 9, 2008

(87) PCT Pub. No.: WO2007/058391

PCT Pub. Date: May 24, 2007

(65) Prior Publication Data

US 2009/0151457 A1 Jun. 18, 2009

(30) Foreign Application Priority Data

Nov. 21, 2005 (JP) ............................. 2005-335184
Nov. 20, 2006 (JP) ............................. 2006-312782

(51) Int. Cl.
*G01N 9/24* (2006.01)
(52) U.S. Cl. .............................. 73/622; 73/624; 73/628
(58) Field of Classification Search ........... 73/598–600, 73/602, 619–622, 624, 625, 627, 628
See application file for complete search history.

(56) References Cited

U.S. PATENT DOCUMENTS 3,302,453 A * 2/1967 Wood et al. ................ 73/622

(Continued)

FOREIGN PATENT DOCUMENTS

JP 56-067750 A 6/1981

(Continued)

OTHER PUBLICATIONS

Y. Iizuka et al: Non-Destructive-Inspection Technologies for Steel-Pipe Products, JFE Giho, No. 9, Aug. 2005, pp. 40-45.

(Continued)

*Primary Examiner*—Hezron Williams
*Assistant Examiner*—Samir M Shah
(74) *Attorney, Agent, or Firm*—Frishauf, Holtz, Goodman & Chick, P.C.

(57) ABSTRACT

Disclosed are an ultrasonic testing system and an ultrasonic testing technique for a pipe member capable of detecting minute flaws of several hundreds of microns or less located at positions in the wall thickness inside portion of a welded portion of a seam-welded pipe and the like without omission and further easily setting optimum conditions when the size of the pipe is changed. A transmitting beam, which is focused to the welded portion at an oblique angle, is transmitted using a part of the group of transducer elements of a linear array probe as a group of transducer elements for transmission, a receiving beam, which is focused at the focusing position of the transmitting beam at an oblique angle, is formed using the transducer elements of a portion different from the above group of transducer elements for transmission as a group of transducer elements for reception, and a flaw echo is received from the welded portion.

16 Claims, 18 Drawing Sheets

U.S. PATENT DOCUMENTS

| | | | |
|---|---|---|---|
| 3,739,628 A * | 6/1973 | Saglio | 73/627 |
| 3,868,847 A * | 3/1975 | Gunkel | 73/622 |
| 3,914,986 A * | 10/1975 | Ota et al. | 73/611 |
| 4,088,029 A * | 5/1978 | Yamamoto et al. | 73/612 |
| 4,160,386 A * | 7/1979 | Jackson et al. | 73/625 |
| 4,193,306 A * | 3/1980 | Flaherty et al. | 73/629 |
| 4,270,389 A * | 6/1981 | Shiraiwa et al. | 73/612 |
| 4,375,165 A * | 3/1983 | de Sterke | 73/622 |
| 4,406,167 A * | 9/1983 | Maeda | 73/622 |
| 4,480,475 A * | 11/1984 | Tsao et al. | 73/610 |
| 4,531,409 A * | 7/1985 | Koch et al. | 73/588 |
| 4,627,289 A * | 12/1986 | Fukuda et al. | 73/622 |
| 4,742,713 A * | 5/1988 | Abe et al. | 73/620 |
| 5,005,420 A * | 4/1991 | Miyajima | 73/629 |
| 5,583,292 A * | 12/1996 | Karbach et al. | 73/638 |
| 5,777,229 A * | 7/1998 | Geier et al. | 73/624 |
| 6,072,144 A * | 6/2000 | Perryman | 219/109 |
| 6,125,705 A * | 10/2000 | Johnson | 73/622 |
| 6,484,584 B2 * | 11/2002 | Johnson et al. | 73/624 |
| 6,684,706 B2 * | 2/2004 | Knight et al. | 73/623 |
| 6,848,312 B2 * | 2/2005 | Georgeson | 73/627 |
| 6,957,583 B2 * | 10/2005 | Tooma et al. | 73/625 |
| 6,993,971 B2 * | 2/2006 | Bossi et al. | 73/620 |
| 7,204,147 B2 * | 4/2007 | Fujimoto et al. | 73/627 |
| 7,236,255 B2 * | 6/2007 | Kodama et al. | 356/601 |
| 7,471,400 B2 * | 12/2008 | Kodama et al. | 356/601 |
| 2001/0052264 A1 * | 12/2001 | Johnson et al. | 73/628 |
| 2004/0118210 A1 * | 6/2004 | Tooma et al. | 73/625 |
| 2005/0126294 A1 * | 6/2005 | Bossi et al. | 73/629 |
| 2006/0191343 A1 * | 8/2006 | Fujimoto et al. | 73/627 |
| 2007/0253519 A1 * | 11/2007 | Meier et al. | 376/260 |
| 2008/0037695 A1 * | 2/2008 | Kono et al. | 376/249 |
| 2009/0095087 A1 * | 4/2009 | Yamano | 73/622 |

FOREIGN PATENT DOCUMENTS

| | | | |
|---|---|---|---|
| JP | 60-205356 A | | 10/1985 |
| JP | 61-111461 A | | 5/1986 |
| JP | 62-108865 U | | 7/1987 |
| JP | 04-274756 A | | 9/1992 |
| JP | 07-035729 A | | 2/1995 |
| JP | 11-183446 A | | 7/1999 |
| JP | 2003329582 A | * | 11/2003 |

OTHER PUBLICATIONS

International Search Report (in the English and Japanese languages) dated Feb. 20, 2007, issued in a counterpart International Application.

* cited by examiner

FIG. 16A CONVENTIONAL METHOD

FIG. 16C PRESENT INVENTION

FIG. 16E TO-BE-TESTED MEMBER $\theta a = 90 - \theta$
$\theta b = \theta$ (b) TRANSVERSE WAVE → TRANSVERSE WAVE $\theta a = 90 - \theta - \theta 1$
$\theta b = \theta + \theta 2$

ULTRASONIC TESTING SYSTEM AND ULTRASONIC TESTING TECHNIQUE FOR PIPE MEMBER

This application is a U.S. National Phase Application under 35 USC 371 of International Application PCT/JP2006/323636 filed Nov. 21, 2006.

TECHNICAL FIELD

The present invention relates to an ultrasonic testing system and an ultrasonic testing technique for a pipe member for accurately detecting minute flaws occurring to a welded portion of a welded steel pipe by ultrasonic testing.

TECHNICAL FIELD

In a welded steel pipe, the quality of a welded portion is very important, and on-line flaw testing of a welded portion is ordinary carried out by angle beam testing in a manufacturing process. In the technique, an ultrasonic wave is obliquely incident on a surface to be tested of a to-be-tested member, and the flaws of the inside and outside surfaces and the internal flaws of the to-be-tested member are detected from the echo reflected from the flaws. Ordinarily, a reflection technique using an ultrasonic beam of 5 MHz having an angle of refraction of 45° is applied to, for example, a seam-welded pipe, and flaws of the order of millimeters, for example, incomplete penetrations, burn through, cracks due to inclusion, and the like are detected.

In contrast, recently, since very severe quality is required to a welded steel pipe, it is required to detect flaws smaller than conventional ones. For example, it is required to detect cold joint flaws and minute penetrators in a seam-welded pipe and to detect blow holes and the like in a laser welded pipe, and these flaws have a very small size of several tens to several hundreds of micron meters. Further, as a position of occurrence of flaws, they may occur in any location from an inside surface to an outside surface along a welding line, and the point of incidence of an ultrasonic beam is different from the point of return thereof depending on the position a flaw. Since flaws are not detected often by ultrasonic testing techniques used practically up to now due to the influence of them, a technique capable of detecting flaws more accurately is required.

The following conventional techniques are disclosed as techniques of detecting minute flaws of a welded steel pipe. Patent Document 1 improves a penetrator detection capability in an angle beam testing by using a point focus probe having a frequency of at least 8 MHz. Further, Patent Document 2 improves a detection capability by forming a focus beam by an array probe so that blow holes can be detected by scanning from the inside surface to the outside surface of a welded portion by a sector scan.

Further, Patent Document 3 detects cold joint flaws, which are mixed as a group of minute FeO of several micron meters or less, by causing an ultrasonic wave to be incident on a welded portion from the outside surface of a pipe at an angle of incidence of 0° or more to 20° or less while setting the frequency of the ultrasonic wave from 25 MHz or more to 500 MHz or less. Further, Patent Document 4 detects blow holes of 0.1 mm or more using a plurality of point focus probes, which have a frequency of from 20 MHz to 80 MHz and are disposed such that a focusing position has a pitch of 3 mm or less from just above a seam.

Note that since the following Patent Document 5 is cited in "Disclosure of the Invention", it is also shown here.

Patent Document 1: Japanese Unexamined Patent Application Publication No. 60-205356
Patent Document 2: Japanese Unexamined Patent Application Publication No. 11-183446
Patent Document 3: Japanese Unexamined Patent Application Publication No. 61-111461
Patent Document 4: Japanese Unexamined Patent Application Publication No. 7-35729
Patent Document 5: Japanese Unexamined Patent Application Publication No. 4-274756

However, the problems described below still remain even in the techniques disclosed above. First, the technique of Patent Document 1 has a problem in that many channels are necessary to detect the flaws in the entire area in the depth direction of a welded portion (wall thickness direction of steel pipe) without omitting them because the beam width of a focused ultrasonic wave is narrow and thus an equipment cost becomes expensive and further in that when a pipe size is changed, a position adjustment and the like are troublesome. Further, when a flaw is not a blowhole shape and is a plane shape as that in a penetrator and a cold joint as well as a flaw is located in a wall thickness inside portion, it is difficult to detect the flaw because an echo travels in a direction different from a direction of incidence.

Further, in the technique of Patent Document 2, since only one array probe is necessary as well as setting can be electronically carried out when a size is changed, it can overcome the former problem shown in Patent Document 1. However, the latter problem still remains unsolved.

Further, when a flaw shape is a plane shape as described above, since an upset is applied to a seam portion, in, for example, a seam-welded pipe, a flaw has a very narrow width of 100 µm or less when viewed from just above a seam. Accordingly, an echo from the flaw is actually very weak even in the techniques of Patent Documents 3 and 4, and thus it is often difficult to detect the flaw. Further, since an area of about 1 to 2 mm in the vicinity of a surface echo is made to a dead zone by a reverberant surface echo, a problem arises in that when a flaw is located in the vicinity of an outside surface, it cannot be detected.

As described above, a technique for detecting minute flaws of about several hundreds of micron meters or less, which occur in a-welded portion of a welded steel pipe in a pipe-axial direction, nondestructively, accurately, stably, and online, is not yet established except a C-scan technique for detecting it offline by a sample cut out from the welded portion.

DISCLOSURE OF THE INVENTION

An object of the present invention, which was made in view of the above circumstances, is to provide an ultrasonic testing system and an ultrasonic testing technique for a pipe member having a first object of detecting minute flaws of about several hundreds of micron meters or less, which occur in the wall thickness inside portion of a welded portion of a welded steel pipe and the like from an inside surface to an outside surface without omitting them and a second object of easily setting optimum conditions when a pipe size is changed.

To solve the above problems, the following means are specifically provided.

A first invention of the present invention is an ultrasonic testing system for a pipe member characterized by including a transmitting/receiving unit having a transmitting unit, which transmits an ultrasonic wave to the welded surface of a welded portion in a pipe axis direction of a pipe member and to the inside surface of the pipe member so that the ultrasonic wave is incident at an angle within the range from 33.2° to 56.8°, respectively, and a receiving unit, which partly or entirely receives an echo reflected in a direction within the range from −12° to 16° to the mirror reflecting direction in the welded surface, wherein the transmitting unit and the receiving unit are composed of different groups of transducer elements on one, two, or more array probes disposed in a pipe member peripheral direction, and a controller for scanning the pipe member in a thickness direction by carrying out a control to change the groups of transducer elements corresponding to the transmitting unit and the receiving unit on the array probe or to change the angle of the array probe as well as controlling the angle of incidence of the ultrasonic wave to the pipe member in the respective transmitting and receiving waves so that the angles of incidence to the welded surface and the inside surface and the angle of the echo on the welded surface are kept within the ranges defined as to the transmitted wave and the received wave, respectively.

A second invention of the present invention is an ultrasonic testing system for a pipe member in the ultrasonic testing system of the first invention which is characterized in that the controller controls an angle of incidence to the pipe member and a focus position by offsetting at least one of timing of wave transmission and timing of wave reception of the respective transducer elements in the group of transducer elements so that the angles of incidence to the welded surface and the inside surface and the angle of the echo on the welded surface are kept within the defined ranges, respectively.

A third invention of the present invention is an ultrasonic testing system for a pipe member in the ultrasonic testing system of the first invention which is characterized in that the angle of incidence of at least one of the ultrasonic wave on the transmitting side or the ultrasonic wave on the receiving side to the pipe member is kept to a predetermined angle.

A fourth invention of the present invention is an ultrasonic testing system for a pipe member in the ultrasonic testing system of the third invention which is characterized in that the controller controls at least one of the wave transmitted from or received by the respective transducer elements so that the angle of incidence of the ultrasonic wave to the pipe member is made to a predetermined angle.

A fifth invention of the present invention is an ultrasonic testing system for a pipe member in the ultrasonic testing system of the fourth invention which is characterized in that the controller controls the angle of incidence to the pipe member and the focus position by offsets at least one of timing of wave transmission and timing of wave reception of the respective transducer elements in the group of transducer elements based on a curvature of the pipe member.

A sixth invention of the present invention is an ultrasonic testing system for a pipe member in the ultrasonic testing system of the third invention which is characterized in that the array probe provides the group of transducer elements with a curvature so that they are disposed along the peripheral direction of the pipe member.

A seventh invention of the present invention is an ultrasonic testing system for a pipe member in the ultrasonic testing system of the first invention which is characterized in that at least one of the transmitting unit or the receiving unit transmits an ultrasonic wave having a focusing coefficient of 5 dB or more to 50 dB or less.

An eighth invention of the present invention is an ultrasonic testing system for a pipe member in the ultrasonic testing system of the first invention which is characterized in that the array probe includes an acoustical lens for focusing the transmitting beam and the receiving beam in the pipe axis direction of the pipe member, and the focal length of the acoustical lens is set shorter as it is nearer to the welded portion and longer as it is farther from the welded portion.

A ninth invention of the present invention is an ultrasonic testing system for a pipe member in the ultrasonic testing system of the first invention which is characterized in that the transmitting/receiving unit comprises a plurality of array probes as well as includes a transmitting unit and a receiving unit on each array probe.

A tenth invention of the present invention is an ultrasonic testing system for a pipe member in the ultrasonic testing system of the first invention which is characterized in that the transmitting unit and the receiving unit of the transmitting/receiving unit comprises different array probes.

An eleventh invention of the present invention is an ultrasonic testing system for a pipe member in the ultrasonic testing system of the first invention which is characterized in that the transmitting unit and the receiving unit of the transmitting/receiving unit comprises different array probes and the controller changes the deflection angles of the transmitting beams and the receiving beams from the respective array probes.

A twelfth invention of the present invention is an ultrasonic testing system for a pipe member in the ultrasonic testing system of the first invention which is characterized in that the controller changes the angle of incidence and the focus position of the ultrasonic wave to the pipe member in at least one of the transmitting wave or the receiving wave so that the scanning lines of the transmitting beam intersect the scanning lines of the receiving beam at a plurality of positions.

A thirteenth invention of the present invention is an ultrasonic testing technique for a pipe member which is characterized in that the ultrasonic testing technique uses an ultrasonic testing system for a pipe member comprising a transmitting unit and a receiving unit composed of different groups of transducer elements on one, two, or more array probes disposed in a pipe member peripheral direction and has transmitting an ultrasonic wave to the welded surface of a welded portion in a pipe axis direction of the pipe member and to the inside surface of the pipe member by the transmitting unit so that the ultrasonic wave is incident at an angle within the range from 33.2° to 56.8°, respectively, partly or entirely receiving an echo reflected in a direction within the range from −12° to 16° to the mirror reflecting direction in the welded surface, and scanning the pipe member in a thickness direction by carrying out a control to change the groups of transducer elements corresponding to the transmitting unit and the receiving unit on the array probe or to change the angle of the array probe.

A fourteenth invention of the present invention is an ultrasonic testing technique for a pipe member in the ultrasonic testing technique of the thirteenth invention which is characterized by having controlling the angle of incidence to the pipe member and a focus position by offsetting at least one of timing of wave transmission and/or wave reception of the respective transducer elements in the group of transducer elements.

A fifteenth invention of the present invention is an ultrasonic testing technique for a pipe member in the ultrasonic testing technique of the thirteenth invention which is characterized by having keeping the angle of incidence of at least one of the ultrasonic wave on the transmitting side or the ultrasonic wave on the receiving side to the pipe member is kept to a predetermined angle.

A sixteenth invention of the present invention is an ultrasonic testing technique for a pipe member in the ultrasonic testing technique of the thirteenth invention which is characterized in that at least one of the transmitting unit and/or the receiving unit transmits an ultrasonic wave having a focusing coefficient of 5 dB or more to 50 dB or less.

BRIEF DESCRIPTION OF THE DRAWINGS

FIGS. 16A to 16E are view showing a comparison example between a conventional technique employing a nontandem arrangement and a tandem testing technique.

BEST MODE FOR CARRYING OUT THE INVENTION

Figure 1:
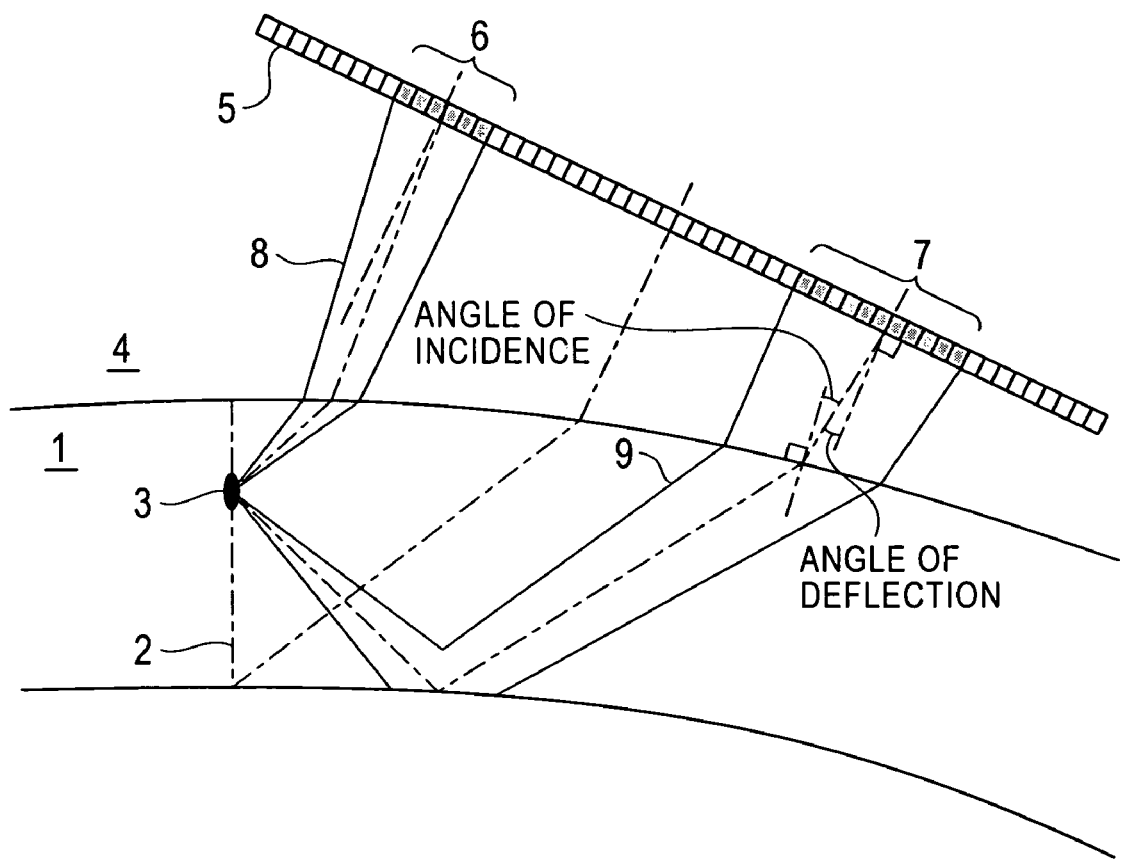
FIG. 1 is a view explaining a first embodiment of the present invention.

The mechanical characteristics of a seam-welded steel pipe are greatly influenced by the existence of minute flaws such as a penetrator and the like in the welded surface of the steel pipe in a pipe axis direction. Thus, the inventors have developed a technique capable of detecting even minute flaws of about hundreds of micron meters or less and sometimes of one hundred micron meters or less nondestructively and online by analyzing reflection characteristics in minute flaws and analyzing complex transmission paths in a steel pipe having a curvature.

First, the inventors investigated the flaw characteristics of a penetrator and found that when an ultrasonic wave was caused to be incident on a welded surface and the echo of the ultrasonic wave was detected at an angle in the vicinity of a mirror reflecting direction, a signal could be detected very sensitively with respect even to a minute flow of about hundreds of micron meters or less by paying attention to that the penetorator had a flat shape, which was thin in a pipe peripheral direction and expanded in a welded surface in a pipe axis direction orthogonal to the pipe peripheral. Accordingly, the inventors examined to arrange a transmission/reception probe, which was not ordinarily used to an ultrasonic wave testing of a steel pipe, as a tandem probe (a transmitting position was set at a position spaced apart from a receiving position), and reached the present invention which could continuously carrying out testing online by making use of the array probe even if it is arranged as the tandem probe.

However, it is not easy to apply the tandem arrangement, in which a transducer element for transmission and a transducer element for reception are disposed at different positions as described above (different groups of transducer elements were used in an array probe) to a steel pipe having a curvature, although it can be relatively easily applied to a flat steel plate. Although the present invention aims at a technique capable of detecting a minute flaw highly sensitively by the tandem arrangement, it is important to maintain sensitivity improved by the tandem arrangement without deteriorating it. To realize it, occurrence of a mode-conversion loss should be prevented which is a phenomenon that when a transverse ultrasonic wave is reflected on the inside and outside surfaces of a steel pipe or at a flaw, a part of the transverse ultrasonic wave is converted into a longitudinal ultrasonic wave and attenuated.

However, when the array probe is disposed in the peripheral direction of a steel pipe as it is, if the position of a transmitting unit on an array or the position at which the ultrasonic wave is incident on the steel pipe change, the angle of incidence of the ultrasonic wave to the pipe member having a curvature also changes. Accordingly, a refraction index also changes, and thus the angle of incidence and the angle of outgoing of the ultrasonic wave also change when they are reflected on the inside and outside surfaces of the steel pipe or at the flaw. Thus, there is a possibility that a logical range, in which the mode-conversion loss is not caused, may be deviated depending on conditions.

Although the angle of incidence itself is not important here and what is important is the value itself of the angle of refraction corresponding to the angle of incidence, a desired angle of refraction can be obtained by controlling the angle of incidence. The present invention is arranged such that even if a subject, to which an ultrasonic testing system having the tandem arrangement is applied, is a pipe member, an angle of refraction is set within the logical range, in which the mode-conversion loss is not caused, by controlling the angle of incidence in consideration of the curvature of the pipe member.

In another aspect of the present invention, a further idea is added when the tandem array probe is applied to a pipe member having a curvature. First, since an ordinary array probe is formed in a linear shape and disposed around a peripheral surface, the relative angle between the group of transducer elements of the array probe and the outside surface of a pipe changes in a peripheral direction. That is, when the group of transducer elements, which constitutes a transmitting unit and a receiving unit, is moved by changing the positions thereof on the array probe to scan a welded portion, if an ultrasonic wave is emitted such that the scanning line angles of transmitting beams transmitted from the group of transducer elements and receiving beams received thereby have a predetermined angle to the surface of the array probe, the angle of incidence of a certain transmission/reception to the pipe member is different from that of another transmission/reception thereto. Accordingly, the ultrasonic wave has a different angle of refraction and a different angle of reflection when it is transmitted thereafter in the pipe member. That is, a problem arises in that when the ultrasonic wave passes through a transmission path after it is incident on a pipe, it is not reflected on a welded portion of the pipe and is reflected on the outside surface thereof after it is reflected on the inside surface thereof or the ultrasonic wave outgoing from the pipe passes through a position outside of the range of the array probe depending on the condition of an angle of incidence.

As described above, in the scanning technique of the flat steel plate employing the array probe, it is difficult to dispose the transmitting unit and the receiving unit at appropriate positions on the array probe in a pipe member having a curvature. The inventors conceived that this difficulty could be overcome by keeping the angle of incidence of any one of a transmission side and a reception side or preferably both the transmission and reception sides to a predetermined angle through scanning. With this arrangement, the angle of refraction in the pipe member could be kept to a predetermined angle, the positional relationship between the transmitting unit and the receiving unit can be determined geometrically even in the pipe member, and the transmitting unit and the receiving unit could be disposed at appropriate positions. Note that, as a means for keeping the angle of incidence to the predetermined angle, it is sufficient to control the wave transmission of the respective transducer elements of a group of transducer elements constituting the transmitting unit or to form the curvature of a linear array itself approximately similar to that of the pipe member, which will be explained later in detail.

A still another aspect of the present invention resides in that the inventors found a focusing condition for realizing sensitivity higher than a predetermined level. In the conventional techniques, which did not employ the tandem arrangement, even if a degree of beam focusing was increased, a sufficient focusing effect could not be confirmed due to disturbance noise existing originally. In contrast, in the present invention, it could be confirmed that the beam focusing effect of an ultrasonic wave could be sufficiently exhibited because the influence of disturbance noise and the like were eliminated by receiving a mirror-echo on a welded surface by the tandem arrangement. In view of the outstanding focusing effect, the inventors found that even a penetrator having a height (size in a pipe wall thickness direction) of about several hundreds of micron meters could be measured within the range of restriction of the current hardware and specified a detecting condition of it. The detecting capability has a sufficient detecting capability even when a minute flaw of about 100 µm or less of the present invention is detected, and thus it belongs to a high performance.

First, the inventors investigated the reflection characteristics of a flaw to be detected and determined the optimum ranges of the angle of incidence of an ultrasonic wave incident on a flaw and the angle of reflection of the ultrasonic wave at which the echo reflected on the flaw is received to detect a minute flaw, which will be described below in detail.

[Analysis of Reflection Characteristics of Flaw]

It is assumed that a minute flaw such as a penetrator, a cold joint flaw, and the like, which exist in a welded portion of a seam-welded steel pipe as a subject of the present invention is collapsed in a pipe peripheral direction and made thin, whereas it is extended in a pipe thickness (pipe diameter) direction and in a pipe axis direction, that is, in a welded surface in the pipe axis direction because the seam-welded steel pipe is manufactured by upsetting the welded portion.

Figure 18A:
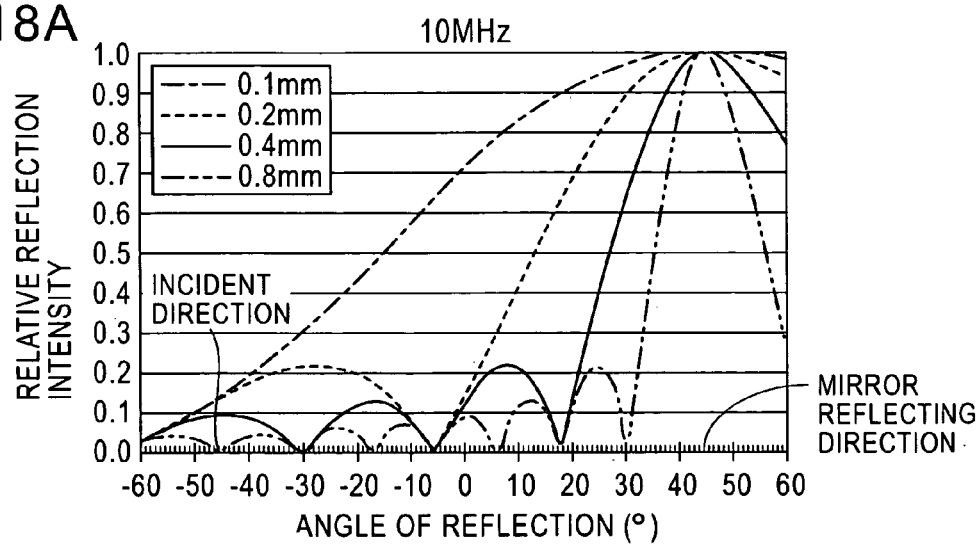
FIGS. 18A to 18C are views explaining the relationship between a flaw size and a reflection directivity.
Figure 18B:
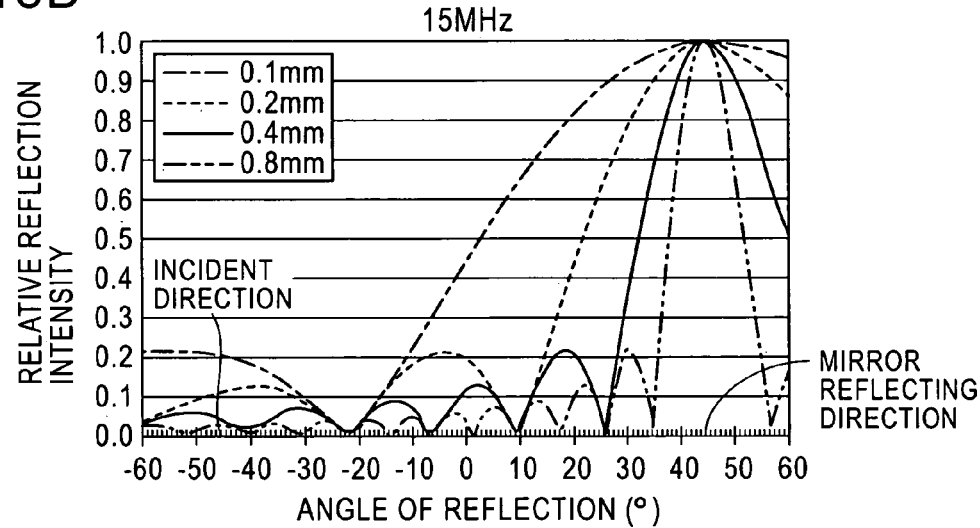
Figure 18C:
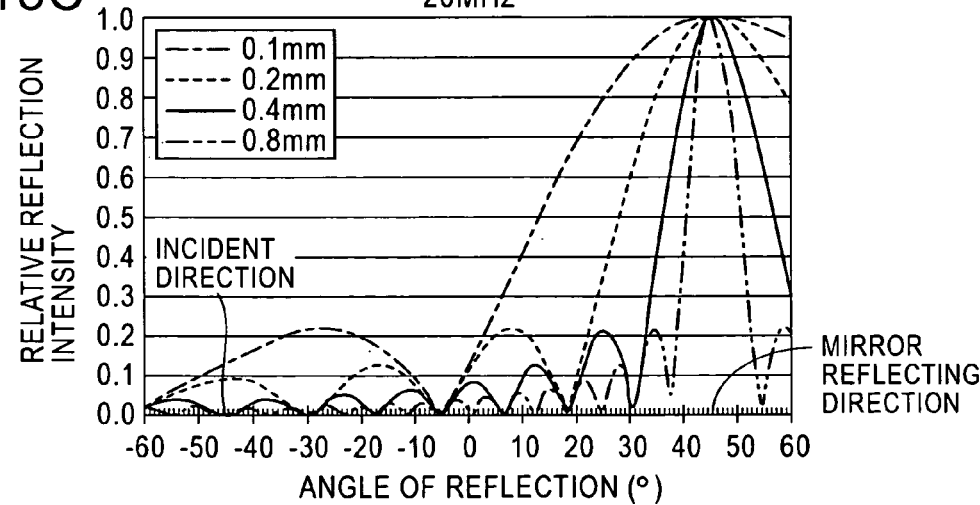
Figure 24:
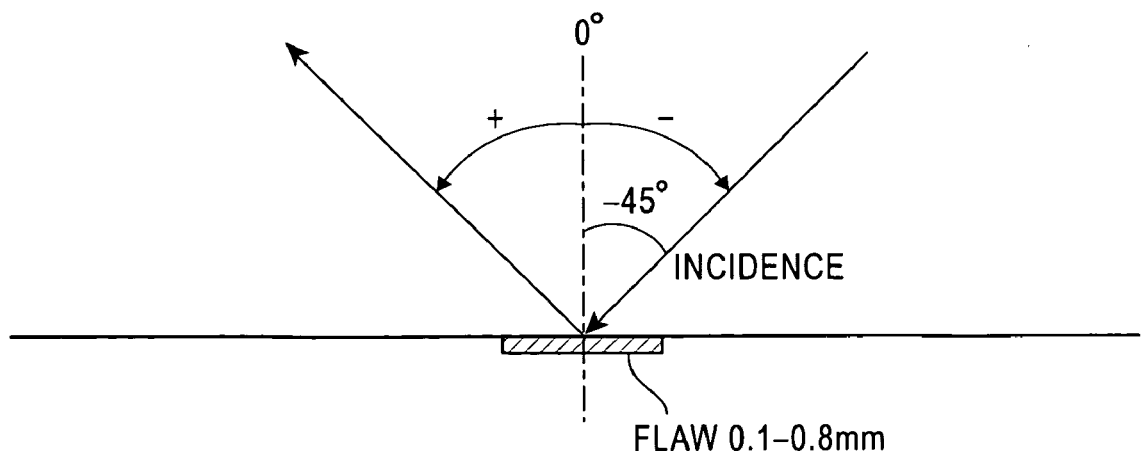
FIG. 24 is view explaining reflection characteristics.

Thus, a result shown in FIG. 18 is obtained by logically examining the relationship between a flaw size and reflection directivity. The result shown in FIG. 18 was obtained by logically calculating signal intensities at respective angles of reflection under the conditions that an ultrasonic wave was incident from a direction of −45° in a frequency of 10 MHz (FIG. 18A), 15 MHz (FIG. 18B), and 20 MHz (FIG. 18C), respectively, and flaws had a size of 0.1 mm, 0.2 mm, 0.4 mm, and 0.8 mm in corresponding to a pipe wall thickness direction (corresponding to a lateral direction in FIG. 24) as shown in FIG. 24. Note that a longitudinal axis of FIG. 18 is shown by a relative value standardized by setting a signal intensity of 45°, which is a mirror reflection angle, to a reference value 1. In any case, the signal intensity of an echo, which is reflected in the −45° direction in which the ultrasonic wave is incident, is very low and about 0.2 or less of that in the mirror reflecting direction. In any case, it can be found that the signal intensity of an echo in the 45° direction, which is the mirror reflecting direction, is most strong.

In the ultrasonic wave with the frequency of 20 MHz whose directivity to a flaw size of 0.8 mm is most acute, an angle at which a signal intensity is reduced to half that of the mirror reflection angle (half a value in FIG. 18) is the range of 40° to 50°. As described above, since the directionality is different depending on a flaw size, it is sufficient to determine an angle of incidence of a receiving beam to a welded portion depending on the size of a flaw desired to be detected. For example, it is preferable that a receiving beam has an angle of incidence near to 45° to a welded portion to detect a larger flaw without the deterioration of sensitivity, and the angle of incidence is preferably within the range of 39°-52° to suppress the reduction of the signal intensity of the flaw of 0.8 mm to half when a frequency is, for example, 15 MHz. Inversely, when a small flaw of 0.4 mm or less is to be detected in, for example, 15 MHz, the range of 33°-61° is also preferable.

It is found by the above analysis that the echo signal of the ultrasonic wave in a flaw has a high signal intensity with a peak in the mirror reflecting direction. It is most preferable to receive an ultrasonic wave in the mirror reflecting direction. However, since a flaw can be sufficiently detected when a reflection intensity is 50% of the peak, it is found that it is sufficient to receive an ultrasonic wave reflected in an angle range corresponding to above range.

Judging from a result of reflection directivity of a flaw size of 0.4 mm in the frequency of 15 MHz shown in FIG. 18B, since a reflection angle at which a reflection intensity is made to 50% or more of the peak is 33-61°, a preferable range is −12° to +16° based on the mirror reflection angle of 45° as the reference. Further, when a flaw size up to 0.8 mm is to be detected in a frequency 20 MHz, a preferable range is −5 to +5° the mirror reflection angle. Further, although the reflection angle characteristics are shown by the angle of incidence of 45° to a flaw in the example described above, the same result can be also obtained as to the angle of incidence characteristics in an angle of reflection of 45° opposite to the above angle. Further, approximately the same characteristics can be obtained even in an angle of incidence other than 45° when it is within the range of an angle of incidence by which the condition of the mode-conversion loss described later is cleared.

Then, the contents of examination of the arrangement of an ultrasonic wave sensor will be explained below based on the flaw reflection characteristics.

[Tandem Arrangement]

According to the knowledge of the flaw reflection characteristics as described above, it is preferable to employ a so-called tandem arrangement for disposing an ultrasonic wave probe for reception at a position different from a position of an ultrasonic wave probe for transmission to receive an ultrasonic wave reflected on a flaw in a predetermined angle range about the mirror reflecting direction. However, when flaws are to be tested without omission in the pipe wall thickness direction (pipe diameter direction) of a welded portion using a point focus probe as disclosed in Patent Document 1, a plurality of probes must be disposed. Further, it is intended to increase an aperture diameter to focus a beam to detect smaller flaws. It is very difficult to realize it as an apparatus arrangement from a viewpoint of engineering and cost.

Thus, the present invention employs tandem arrangement using the array probe. When the array probe is used, the group of transducer elements of the transmitting unit and the group of transducer elements of the receiving unit and/or an angle of refraction in transmission and an angle of refraction in reception are sequentially changed by using the array probe, the focusing position of the ultrasonic wave beam can be scanned from the inside surface to the outside surface of a welded portion in a pipe wall thickness direction (or from the outside surface to the inside surface, that is, the scanning may be carried out in any direction] so that flaws can be tested from the inside surface to the outside surface without a dead zone. Further, since the array probe is used, even if a pipe size is changed, a scanning range and a focusing position can be easily changed, which can carry out a previous adjustment of setting very simply. As described above, the transducer elements of the array probe are selected such that they are disposed in tandem as well as testing without omission can be realized.

Note that the inventors have reached the knowledge that the tandem arrangement is necessary to securely detect minute flaws because it has an sensitivity improvement effect as described below in addition of the improvement of sensitivity obtained by receiving an echo within the predetermined angle range to the mirror reflecting direction.

Figure 15A:
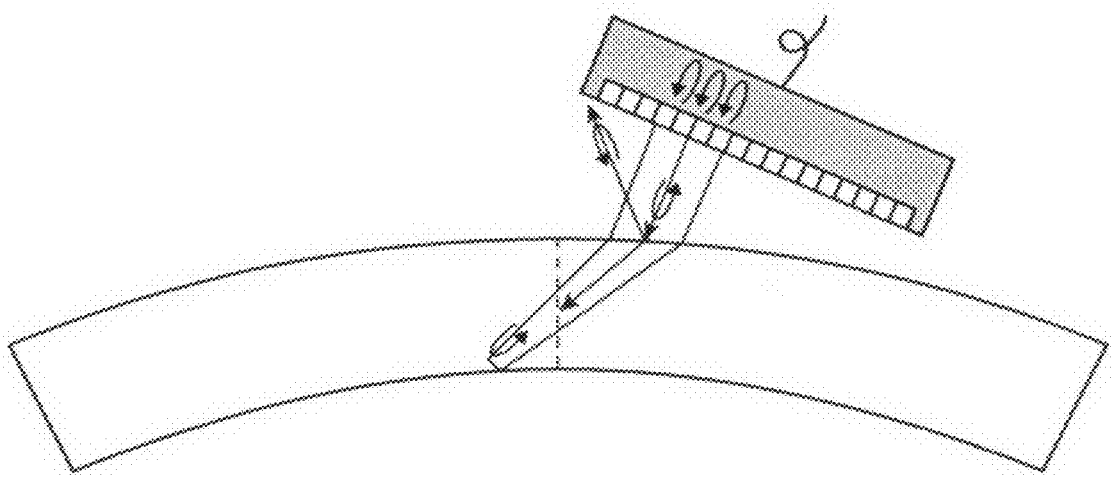
FIGS. 15A and 15B are views schematically showing a comparison between a non-tandem arrangement and a tandem arrangement.

FIG. 15 is a view schematically showing a comparison between a non-tandem arrangement and the tandem arrangement. FIG. 15A shows a case in which a welded portion is tested using an array probe by an ordinary reflection technique having the same transmitting unit and receiving unit. An ultrasonic wave is emitted from a group of transducer elements of the array probe, is incident in a pipe after it is refracted on the outside surface of the pipe, and reaches the welded portion. When a flaw exists, the ultrasonic wave is reflected on it, incident on the same group of transducer elements from which it was emitted through the same path as that through which it was transmitted, and received thereby. When the ultrasonic wave is received, a reverberant sound in the array probe, a diffused echo caused by the surface roughness of the outside surface of the pipe, an echo reflected on the outside surface of the pipe, an echo reflected on the array probe and the holding portion thereof, and the like, and the echo caused by the rough inside surface of the pipe and remaining cut beads travel to the array probe in addition to the echo from the flaw. As described above, in the ordinary reflection technique, since these unnecessary echoes, that is, noises are overlapped with a flaw signal and received, a state in which signal sensitivity and an S/N ratio are bad is detected. Further, it is very difficult to remove the noises.

Figure 15B:
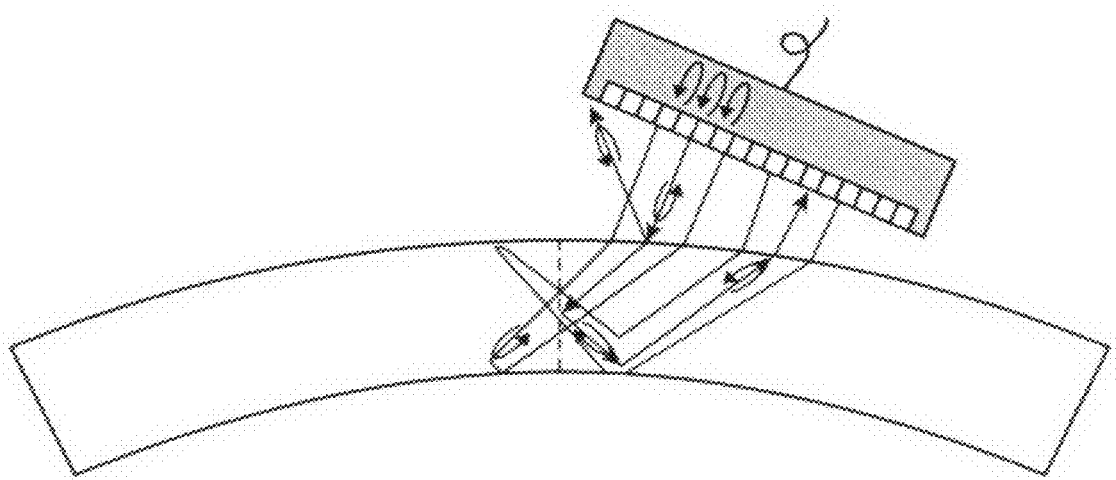

On the other hand, FIG. 15B shows a tandem testing technique employing a tandem arrangement in which different groups of transducer elements for transmission and reception according to the present invention are used.

An ultrasonic wave is emitted from the group of transducer elements for transmission, incident in the pipe after it is refracted on the outside surface of the pipe, and then reaches a welded portion. When a flaw exits, the ultrasonic wave is reflected on the flaw. At the time, the ultrasonic wave most strongly travels in the mirror reflecting direction, is reflected on the inside surface of the pipe, reaches the outside surface of the pipe, is incident on the groups of transducer elements for reception by being refracted after it is refracted, and received thereby.

Since the ultrasonic wave travels the path as described above, a reverberant sound in the array probe, a diffused echo caused by the surface roughness of the outside surface of the pipe, an echo reflected on the outside surface of the pipe, an echo reflected on the array probe and the holding portion thereof, and the like reflected on the outside surface of the pipe, and the echo caused by the rough inside surface of the pipe and remaining cut beads entirely travel to the group of transducer elements for transmission; they do not reach the group of transducer elements for reception. That is, the signal, which is received by the group of transducer elements for reception in the tandem arrangement of the present invention is not overlapped with a noise echo caused by the diffused reflection of an ultrasonic wave and is almost not influenced by the noise. As a result, since an S/N, which is very high as compared with an ordinary reflection technique, can be obtained, an effect of obtaining an echo in the mirror reflecting direction and an effect of reducing noise can be obtained, and thereby a minute flaw can be detected.

FIG. 16 shows an example of a result of testing when the conventional technique, in which the same probe carries out the transmission and the reception without employing the tandem arrangement, is compared with the tandem testing technique according to the present invention.

Figures 16B, 16D:
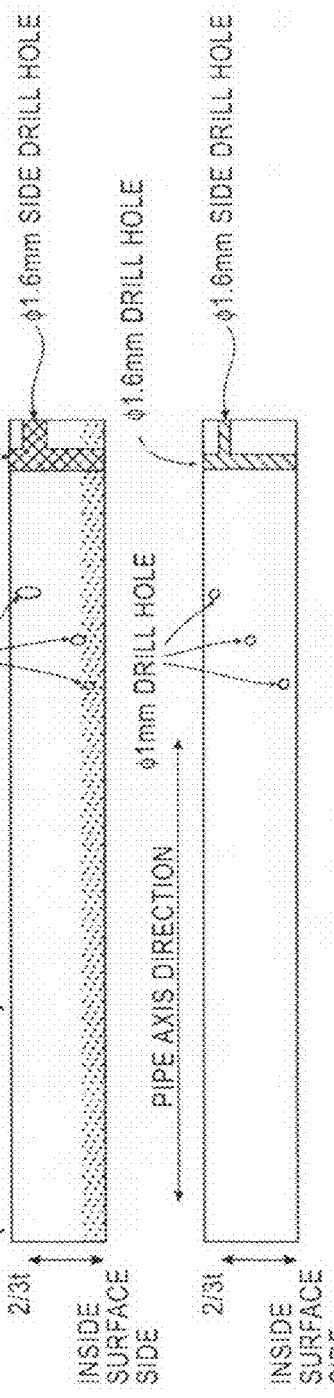
Figure 17A:
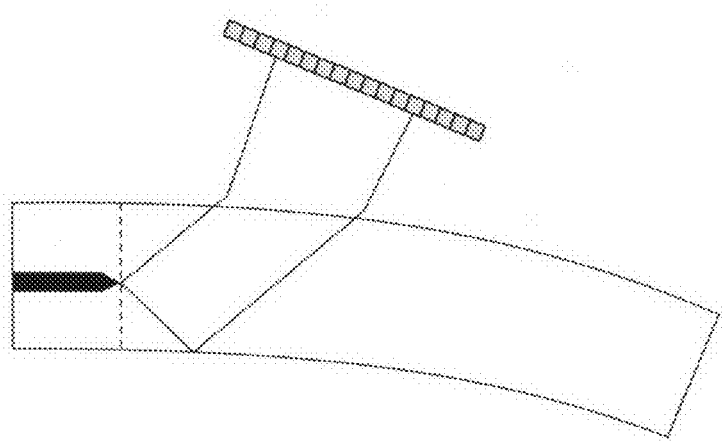
FIGS. 17A to 17C are view explaining drill holes formed to a to-be-tested pipe member.
Figure 17B:
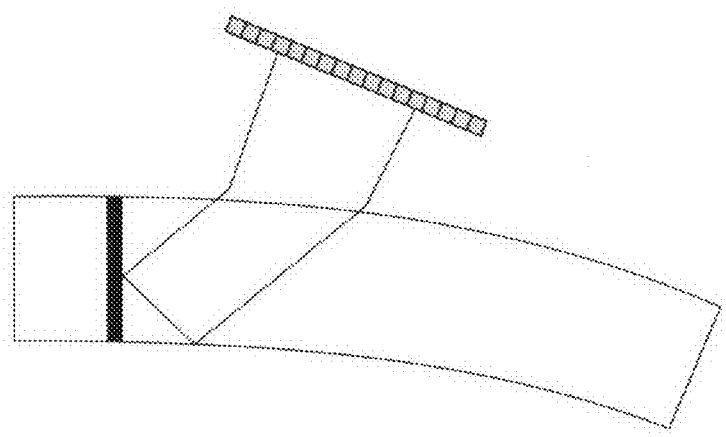
Figure 17C:
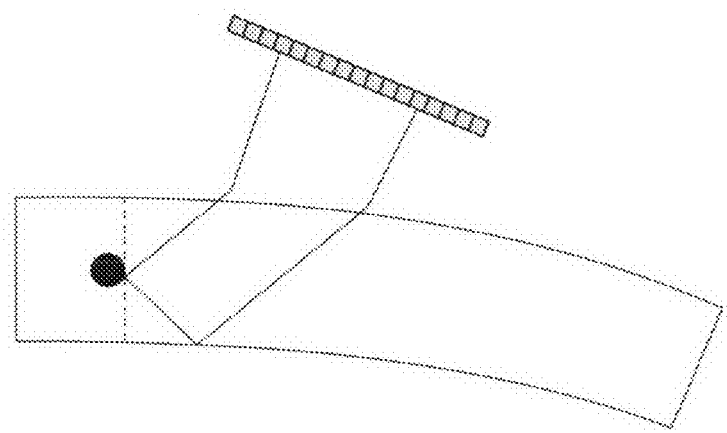

Note that the to-be-tested pipe member used for comparison has three types of drill holes as shown in FIG. 17. That is, the drill holes are a φ1 mm drill hole (FIG. 17A) formed in an orthogonal direction to a surface composed of a wall thickness direction and a pipe axis direction, a φ1.6 mm drill hole passing in the wall thickness direction (FIG. 17B), and a φ1.6 mm drill hole passing in the pipe axis direction (FIG. 17C) at three positions in a different wall thickness direction as shown in FIG. 16E.

FIG. 16A shows image data of a flaw tested by the conventional technique, and FIG. 16C shows image data of a flaw tested by the present invention. FIG. 16B is a view schematically showing FIG. 16A, and FIG. 16D is a view schematically showing FIG. 16C as the image data of the flaw tested by the present invention to explain the flow detecting state of the views of FIGS. 16A and 16C for testing flaws. Note that, in the image data views of FIGS. 16A and 16C, a higher signal intensity is shown more whitish.

As apparent from the above result, in the conventional reflection technique, since noise is strongly generated by surface roughness on the inside surface, the echo from the extreme end the φ1 mm drill hole that simulates a minute flaw [refer to FIG. 17A) is filled with noise, and it is difficult to detect it. In particular, the echo from a wall thickness inside portion is very weak and is not almost detected. On the other hand, in the present invention, noise caused by the surface roughness on the inside surface side is weak and does not influence the echo from the extreme end of the φ1 mm drill hole and can be clearly detected together with the wall thickness inside portion.

As described above, it can be found that the tandem arrangement can improve a detection performance as compared with the conventional technique. However, it is found that the tandem arrangement has several difficulties when it is applied to a pipe member having a curvature. A countermeasure for them will be explained below.

[Examination of Mode-Conversion Loss]

As described above, it has been found that sensitivity can be sufficiently improved by the tandem arrangement. However, to maintain the high sensitivity of the tandem arrangement, occurrence of attenuation of a signal intensity due to a "mode-conversion loss" must be prevented when an ultrasonic wave is reflected on the inside surface and the outside surface of a steel pipe and at a flaw in the transmission process of the ultrasonic wave in the steel pipe. The mode-conversion loss is such a phenomenon that although an ultrasonic wave incident on a steel pipe is a transverse wave, it is converted into a longitudinal ultrasonic wave depending on a reflecting condition with a result that a signal intensity is attenuated and detection sensitivity is deteriorated. The phenomenon will be explained using figures.

Figure 21A:
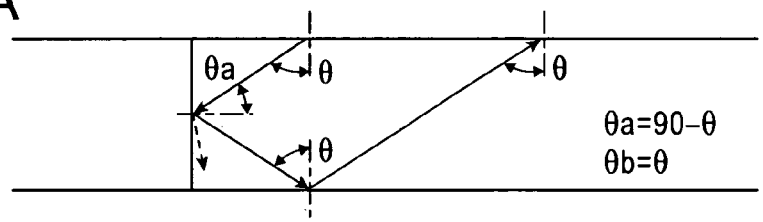
FIGS. 21A to 21C are views explaining a mode-conversion loss of a flat steel plate.
Figure 21B:
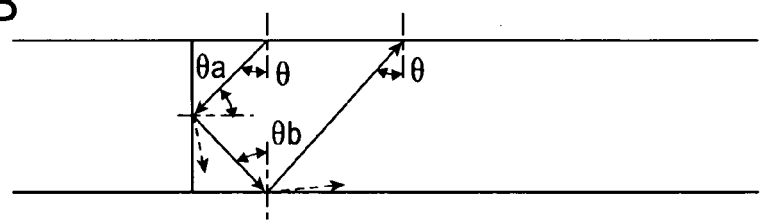
Figure 21C:
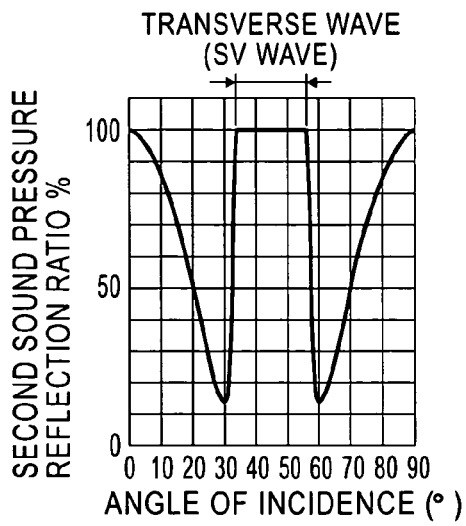

FIGS. 21A to 21C are views explaining the mode-conversion loss in a flat steel plate. FIG. 21A shows testing of the flat steel plate in the tandem arrangement (also described as a tandem testing below). When a transverse ultrasonic wave is incident on the flat steel plate and the angle of refraction thereof is shown by θ, an angle of incidence θa to a welded surface is shown by (90°−θ) in the flat steel plate. Further, an angle of incidence θb to a bottom surface is shown by θ. It is known here that when a transverse ultrasonic wave, which is incident on a steel at an angle of incidence of about 33° or less, is reflected on a welded portion, a bottom surface of a steel plate, and the like, a longitudinal ultrasonic wave is generated in a dotted line direction by mode-conversion due to reflection. When, for example, θ is large (about 57° or more) as shown in FIG. 21A, θa is small (about 33° or less), mode-conversion occurs due to the reflection on the welded portion. Whereas when θ is small (about 33° or less) as shown in 21B, although no mode-conversion occurs due to the reflection on the welded portion, since θb is made to about 33° or less, the mode-conversion occurs. When the mode-conversion from the transverse wave to the longitudinal wave occurs as described above, the intensity of the ultrasonic wave is weakened in a tandem testing direction, thereby the detection sensitivity is deteriorated. As described above, the phenomenon, in which an ultrasonic wave is subjected to the mode-conversion from a transverse wave to a longitudinal wave when it is reflected and the intensity of the transverse ultrasonic wave is attenuated, is called the mode-conversion loss. FIG. 21c shows how a reflection intensity is changed when an ultrasonic wave is reflected twice on a welded surface and an inside surface with respect to the angle of incidence thereof. As shown in FIG. 21c, no mode-conversion loss is occurred within the range of angle of incidence of 33.2° to 56.8° as the logical value.

Note that, in a flat steel plate, the relative angle between an array probe surface and the upper surface of the flat steel plate is fixed regardless of a location. Accordingly, even if a group of transducer elements constituting a transmitting unit and a receiving unit is moved to scan a welded surface with an ultrasonic wave beam, the condition of an angle of refraction indicating whether or not the mode-conversion loss occurs can be easily determined by examining the relative angle between the array probe surface and the upper surface of the flat steel plate and the angle of a transmitting beam to the probe surface at an arbitrary position.

Figure 22A:
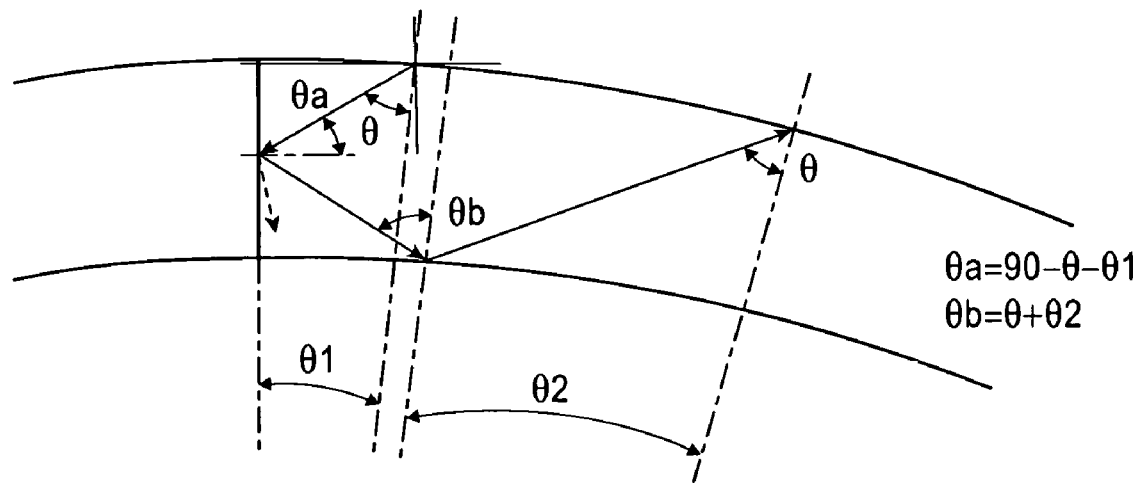
FIGS. 22A and 22B are a view explaining a mode-conversion loss in a steel pipe.

However, in the tandem testing of a steel pipe, the condition of the angle of refraction cannot be easily determined different from the flat steel plate due to the influence of a curvature, which will be explained with reference to FIG. 22. There is contemplated a case that when the angle of a welded surface is set to a reference angle 0° likewise the flat steel plate described above, an ultrasonic wave is incident on a steel pipe from an array probe such that an angle of refraction is set to θ. Note that an incident point (incident position) to the outside surface of the steel pipe is set to a position at which the angle between the normal line direction at the incident point and the welded surface is set to θ1. The angle of incidence θa to the welded surface at the time is not set to (90°−θ) and is set to (90°−θ−θ1). Likewise, an angle of incidence on a bottom surface is not set to θ and is set to (θ+θ2).

In this example, since θ1<θ2, the range of the angle of refraction in which the mode-conversion loss diffraction does not occur is reduced by θ2 at the maximum in comparison with the flat steel plate. As an example, when it is assumed, for example, that an angle of refraction is about 45° in a steel pipe having a wall thickness t and an outside diameter D=3.4%, since θ2 is set to about 4°, the range of the angle of refraction, in which the mode-conversion loss does not occur, is reduced to 37° to 53° when θ2 is caused to correspond to the angle of refraction. Note that judging from an actually available steel pipe size, θ2 is set within the range of about 1.7° to 11.25°. Note that, judging from an actually available steel pipe size, θ2 is set within the range of about 1.7° to 11.25°. Note that a considerable portion of leading steel pipe sizes can be covered in the range from a minimum t/D value to t/D=5%, and when t/D=5%, θ2 is set to 6.8°. In this case, the range of the angle of refraction is set to 40° to 50°.

Figure 22B:
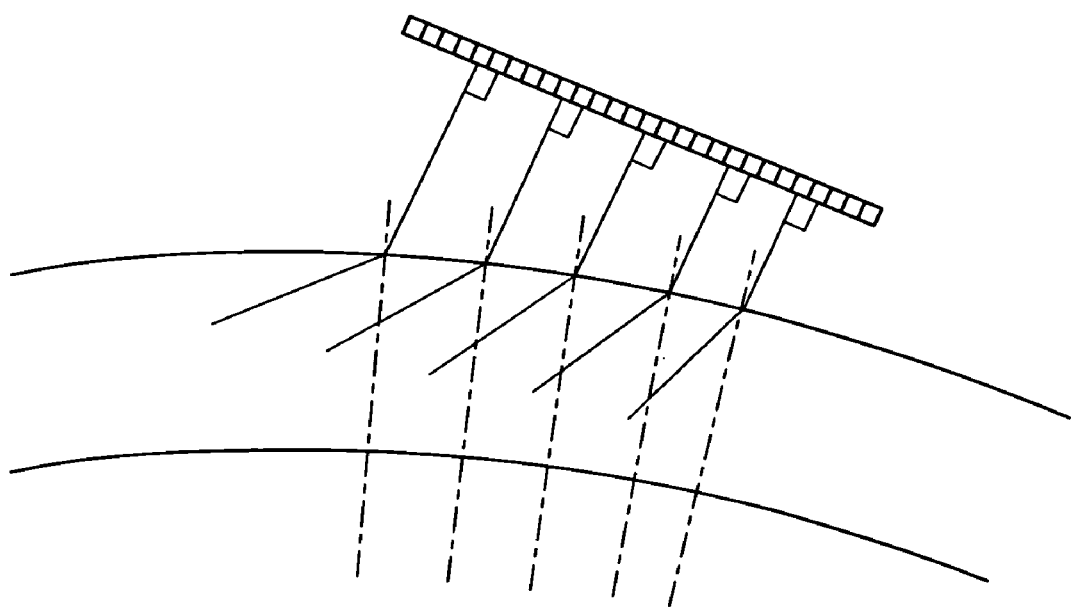

Further, when it is taken into consideration that the array transducer elements are generally formed in a linear shape and that a steel pipe has a curvature, if an ultrasonic wave beam is transmitted at a predetermined angle (in the figure, at 90° with respect to a probe surface) from array transducer elements likewise the flat steel plate as shown in FIG. 22B, an angle of incidence on the steep pipe is not set to a predetermined angle, and thus an angle of refraction is not also set to a predetermined angle. To carry out the tandem testing, when the width of a beam scan from the transducer elements is set twice the wall thickness in the above steel pipe of t/D=3.4% as an example, even if a probe is disposed such that an angle of refraction is set to 45° at a center, the angle of refraction changes from 31° to 62° within the scan width and thus exceeds the range in which the mode-conversion loss does not occurs.

Accordingly, unless a beam is controlled such that an angle of refraction is set within a predetermined range in which the mode-conversion loss does not occur on a welded surface and a bottom surface in consideration of the curvature of the steel pipe in view of the above problem, a steel pipe cannot be subjected to the tandem testing at high sensitivity. When the angle of incidence on the welded surface and on the inside surface of a pipe member is converted into an angle of refraction in consideration of θ2 described above, the angle of refraction is set to 35°-55° with respect to the logical value of the angle of incidence when t/D has a smallest value.

That is, when a measuring position is moved while an ultrasonic wave beam is scanned, the angle of incidence (the angle of refraction) of the ultrasonic wave to the steel pipe is changed. As a result, it cannot be easily determined whether or not an angle at which the mode-conversion loss occurs is achieved, and a technique of determining it is not established.

The inventors has realized to set the angle of incidence at which the mode-conversion loss does not occur by a technique of determining a scanning line as shown below as an example.

A procedure for setting angle of refraction within the range in which the mode-conversion loss does not occur will be explained below.

1) An angle of refraction is determined, and the position and the angle of an array probe are determined.

1)-1: The angle of refraction $\theta$ is determined in consideration of an angle of incidence $\theta a$ on a welded surface. A logical angle of incidence on the welded surface at which the mode-conversion loss does not occur is $33.2° \leq \theta a \leq 56.8°$. When the welded surface is scanned from an inside surface to an outside surface in a pipe wall thickness direction within the range, the angle of incidence on the welded surface need not be a predetermined angle and may change. Accordingly, an example in which the angle of refraction $\theta$ is set to a predetermined angle will be shown here to make a calculation easy. Here, the angle of incidence $\theta a$ on the welded surface is $\theta a=90°-\theta-\theta 1$, and further $\theta 1$ changes within the range of 0 to $\theta 2$ depending on the position in the wall thickness direction of the welded portion (for example, $\theta 1=\theta 2$ on the inside surface side and $\theta 1=0$ on the outside surface side). When, for example, $\theta 2=4°$, and the angle of refraction is 45°, $\theta a=41°$ to 45°. Further, when the angle of refraction is set to 47° at the time an ultrasonic wave is incident on the vicinity of the center of the pipe thickness of the welded portion, $\theta a=$about 45° is established at the center of the welded portion in a wall thickness direction, and $\theta a$ is within the range of 43° to 47° in the scanning of the inside and outside surfaces.

1)-2: The position and the angle of the array probe is determined such that a beam, which is transmitted from the transducer element located at the center of the array probe, is incident from the outside surface side of a steel pipe as a transverse ultrasonic wave at a predetermined angle of refraction (for example, 45°) and is incident on the edge of the welded surface on the inside surface side thereof (or on the outside surface side thereof) at a predetermined angle of incidence (for example, 41° in the example described above).

2) The positions at which the scanning lines transmitted from and received by the respective transducer elements of the array probe are incident on the outside surface of the pipe are determined.

2)-1: Although the positions can be determined by various techniques, they can be determined by, for example, such a technique that the outside surface of a pipe is scanned as to transducer elements as subjects (or a position between the transducer elements), the angle of refraction $\theta$, which is determined by the positions of the transducer elements, the scanning position of the outside surface, and the tangential line of the outside surface, is calculated, and the positions of incidence on the outside surface, at which $\theta$ is set to the value determined in 1)-1, are determined. Specifically, scanning lines are determined by connecting the respective points on the outside surface (for example, the respective points are disposed on an outer periphery at equal intervals or at arbitrary intervals) from the respective transducer elements by straight lines, the angles of refraction $\theta$ of the respective scanning lines are calculated, and the scanning lines which $\theta$ have the same value or a nearest value to a predetermined angle of refraction are selected, thereby the positions of incidence the scanning lines are determined.

2)-2: The transmission paths after the ultrasonic wave is incident on the pipe are geometrically determined from the positions of the transducer elements, the position of incidence on the outside surface determined in 2)-1 described above, and a pipe shape (diameter and thickness), and the position of incidence to the welded surface is determined.

3) Since positioning is carried out at the center of the array probe in 1) described above as well as the above processing is carried out by setting the angle of refraction to the predetermined angle, a combination (pair) of routes of the transmission paths (scanning lines) determined on the welded surface in 2)-2 is symmetrically formed using the scanning line at the center of the array probe as a reference. The pair is used as scanning lines of transmission/reception and used as central transducer elements of respective transmitting and receiving units (groups of transducer elements of the transmitting unit and the receiving unit are mainly composed of the transducer elements). Note that when the number of the groups of transducer elements is an even number, the above processing is carried out by correcting the center position to the boundary of the transducer element. Further, although the calculation is carried out by setting the angle of refraction to the predetermined angle, the calculation may be carried out by setting the angle of incidence $\theta a$ on the welded surface to a predetermined angle, or both $\theta$ and $\theta a$ may be changed.

Although detailed description is made later, when the group of transducer elements is appropriately controlled or the array probe is provided with a curvature, the angle of incidence and the angle of refraction can be set within the logical ranges in which the mode-conversion loss does not occur. Note that although an angle of refraction suitable for testing in the transverse wave can be applied within the range about 30° to 70°, when the angle dependency of the reflection coefficient of sound pressure when the transverse wave is reflected on a flaw and on the inside surface is taken into consideration, the range of about 35° to 55° in which the transverse wave is totally reflected is more preferable. Further, the range may be set to thrust range of 40° to 50° in consideration of stability. Further, although it is most preferable that the angle of refraction of the transmission wave be the same as that of the reception wave, they can be applied even if the angles of refraction of them are different from each other within the range of reflection directivity because the reflection directivity of law is broad.

[Control of Angle of Incidence to Predetermined Angle]

Figure 23:
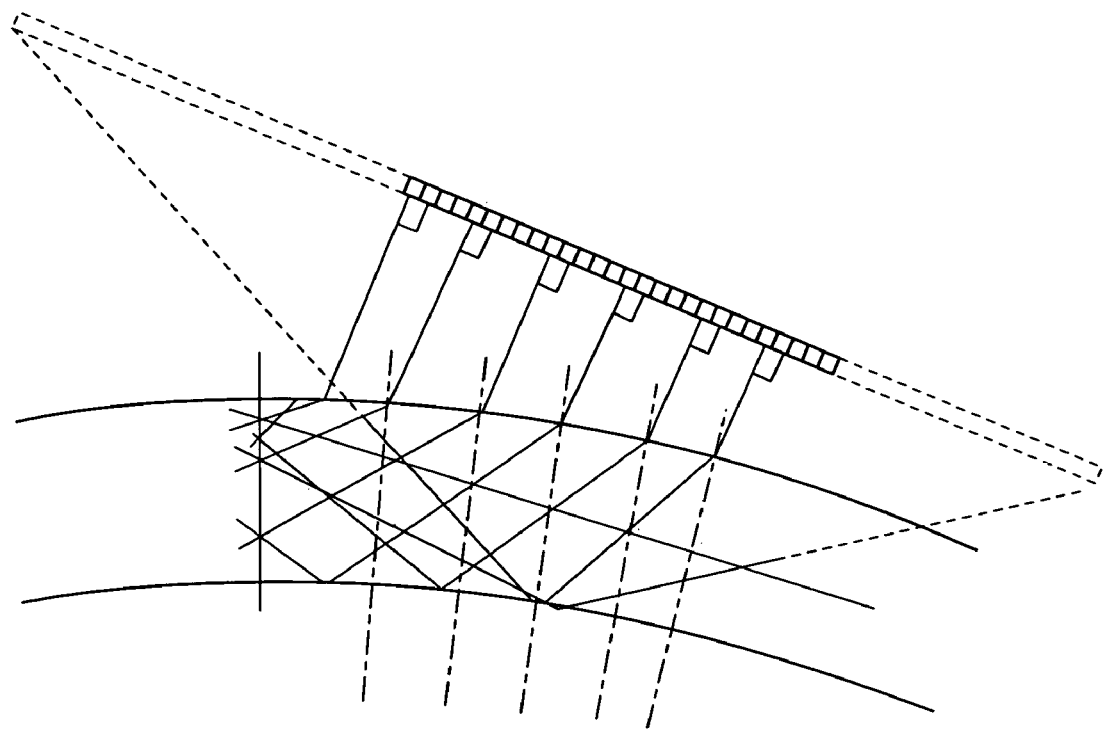
FIG. 23 is a view showing an example a transmission path in a pipe member.

In the application of a tandem array probe to a pipe member having a curvature, when an ordinary linear array probe is disposed around a peripheral surface, if the positions of groups of transducer elements, which constitute a transmitting unit and a receiving unit change on an array, the angle of incidence of a certain transmission/reception on a pipe member is different from that of other transmission/reception thereon. The phenomenon is shown in FIG. 23, which shows an example of transmission paths in a pipe member. It can be found that although transmission and reception are established in the beams shown by thick lines, the relationship between transmission and reception is not established in the beams shown by thin lines other than the above beams because angles of refraction are different.

That is, although the transmitting unit can be accommodated in the array probe, the receiving unit may be located outside of the position of the array probe (shown by broken lines in the figure). Accordingly, the groups of transducer elements of the transmitting unit and the receiving unit cannot be disposed within the range of the array probe in the tandem arrangement. The inventors keep the angle of incidence of any one of the transmission side and the wave reception side or the angles of incidence of both of them to a predetermined angle through scanning. With this arrangement, since the angle of refraction in a pipe member such as a steel pipe and the like is set to a predetermined angle, the problem described above does not almost occur. For example, even if a case of FIG. 4 in which an array probe similar to that of FIG. 23 is used, all the combinations of the transmitting unit and receiving unit are accommodated in the array probe by setting the angle of refraction to the predetermined angle. Further, when the angle of refraction is set to the predetermined angle, there can be also obtained an advantage in that the positional relationship between the transmitted wave and the received wave can be easily determined as long as, for example, both the outside and inside surface sides of a steel pipe are perfect circles. Further, even if the inside surface side of the steel pipe is not the perfect circle because the wall thickness thereof changes, when any of the transmission side and the reception side has a predetermined angle of refraction, the positional relation can be easily determined because the outside surface of the steel pipe is the perfect circle up to the path through which an ultrasonic wave is incident on the welded surface and reflected therefrom. Accordingly, the path ahead of the above path can be also easily determined logically or experimentally in consideration of the shape of the inside surface.

Note that a means for setting the angle of incidence to the predetermined angle can be realized by control the respective transducer elements of the groups of transducer elements used to the transmitting unit and the receiving unit. It is sufficient to select the groups of transducer elements by the technique described above, the other controls will be described later in detail.

Further, as another means, the array probe itself may be arranged in a shape having approximately the same curvature as that of a pipe member and the transducer elements may be controlled thereby.

(Focusing Condition of Ultrasound Wave Beam]

Although a minute flaw such as a penetrator and the like has a low height of several hundreds of micron meters, a reflection intensity can be increased by concentrating a transmitting beam and receiving sensitivity to the flaw by focusing. The inventors derive a condition under which a minute flaw can be detected using a focusing coefficient J shown in an expression (1). The focusing coefficient J is a value showing an increase of sound pressure at a focusing position.

$$J = 20\log\left(\frac{D^2}{4\lambda F}\right) \quad (1)$$

Where, D shows an aperture of a transducer element, F shows a focal length, λ and shows a wavelength. Note that, in the expression (1), values converted in water are used as the focal length F and the wavelength λ.

Figure 3A:
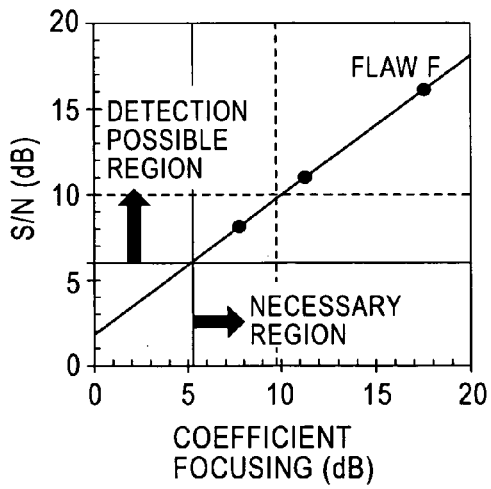
FIGS. 3A and 3B are views showing an example of experiment investigating a focusing capability necessary to the present invention.
Figure 3B:
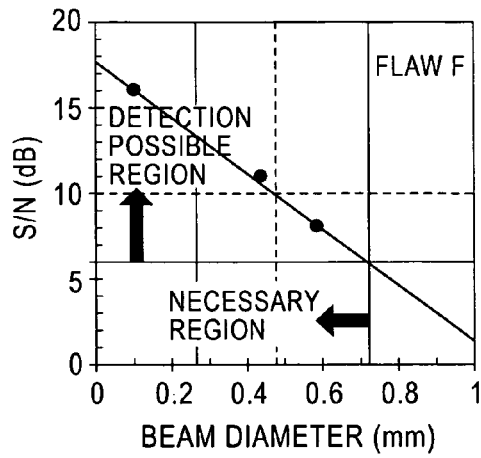

FIGS. 3A and 3B are views showing an example of an experiment which investigated a focusing capability necessary in the present invention. In the experiment, a welded portion of a seam-welded pipe including minute penetrators was subjected to C-scan testing by focusing a seamed portion using point focus probes having various focusing coefficients using samples each sliced to 2 mm across the seam portion. Note that although the range of the focusing coefficients is determined here using a result of the C-scan measurement, the result of the C-scan can be applied as it is to different ultrasonic testing techniques because the focusing coefficients have an advantage in that they can be handled as an index value capable of evaluating the techniques equally.

FIG. 3A shows a result that the relationship between the focusing coefficient and an S/N is determined from the result of the C-scan and shows that a higher focusing coefficient J shows a better S/N of a flaw echo. As a result of observation of a cross section of a flaw F, the height of a flaw F (size in the diameter direction of the steel pipe) is about 100 μm.

In general, at least S/N=6 dB is necessary in online testing, and it is preferable that the S/N be 10 dB or more. Accordingly, it is found from the figure that a necessary focusing coefficient is 5 dB or more and preferably 10 dB or more to detect a flaw similar to the flaw F or a small flaw.

Note that, judging from the reflection characteristics shown in FIG. 18 described above, since a reflection angle corresponds to −45° in the conventional technique employing no tandem arrangement, the reflection intensity, which can be obtained by the technique, is only about 20% of the tandem arrangement. That is, since the sensitivity of the conventional technique is inferior to that of the tandem arrangement by about 14 dB, at least about 20 dB of a focusing coefficient is necessary to obtain an equivalent S/N. Further, when it is taken into consideration that the conventional technique is inevitably influenced by disturbance noise, the focusing coefficient must be more improved. As described above, it can be found that a combination of the tandem arrangement of the present invention and the beam focusing is effective.

Further, FIG. 3B shows a result that the relationship between a beam diameter and an S/N likewise. It can be found from the figure that a necessary beam diameter is 0.7 mm or less and preferably 0.5 mm or less.

Note that the upper limit of the focusing coefficient is 24 dB to 50 dB and the lower limit of the beam diameter is 30 μm to 0.32 mm because the upper limit range of a frequency is about 20 MHz to 50 MHz, the upper limit range of an aperture is about 20 mm to 40 mm, and the lower limit range of a focal length is about 20 mm to 40 mm as the ranges which can be actually realized in angle beam testing of a steel pipe. Note that when the frequency exceeds 20 MHz, since the intensity of an ultrasonic wave signal is greatly attenuated in the transmission in steel, when the upper limit of the frequency is set to 20 MHz, the preferable upper limit range of the focusing coefficient is 40 dB, and the preferable lower limit range of the beam diameter is 74 μm.

When, for example, it is assumed that a water path (length) is 20 mm, a path length in steel is 38 mm, the focal length F is 20 mm+(38 mm/sound speed in water 1480 m/s×sound speed of transverse wave in steel 3230 m/s)=103 mm, and the frequency is 15 MHz, a wavelength λ is 1480 m/s/15 MHz=0.1 mm, and an aperture D for obtaining a focusing coefficient of 10 dB can be determined by the following equation (2).

$$D = \sqrt{10^{\frac{J}{20}} \cdot 4\lambda F} \quad (2)$$

The aperture D determined from the equation (2) is D=11.3 mm. Thus, when the transducer elements of a linear array probe have a pitch of, for example, 0.5 mm, the determined number of the transducer elements of the group of transducer elements is 11.3/0.5=about 22 pieces.

The number of the transducer elements of the group of transducer elements is determined as described above. However, when the number is set to a predetermined value, a problem arises in that since a focal length is made shorter on a side nearer to a welded portion, a beam width is reduced and thus a minute scanning pitch is required, and since the focal length is made longer on a side farther from the welded portion, a focusing capability is deteriorated.

To cope with the above problem, it is preferable to set the number of the transducer elements of the group of transducer elements for transmission smaller on a side nearer to the welded portion and larger on a side farther from the welded portion. With this arrangement, since the aperture is made narrower on a side nearer from the welded portion when excitation is carried out at the same time, the beam width is not extremely reduced even if the focal length is short, and since the aperture is made wider on a side farther from the welded portion when the excitation is carried out at the same time, the focusing coefficient can be increased even if the focal length is long, thereby a detection capability is not deteriorated. Accordingly, since the focusing characteristics from the respective groups of transducer elements can be made uniform, testing can be carried out with uniform detection sensitivity from the inside surface side to the outside surface.

However, since the focusing coefficient includes the focal length F and the aperture D as parameters, when focusing coefficient is set to a predetermined coefficient or within a predetermined range, the sensitivity is not changed by a measuring position determined by scanning, and the aperture can be set according to the focal length. As described above, there is also an advantage that a calculation can be carried out very easily according to the shift of the scanning position by using the focusing coefficient.

Further, when the linear array probe is provided with an acoustical lens and the focal length of the acoustical lens is set shorter on a side nearer to the welded portion and longer on a side farther from the welded portion, a focused transmitting beam and receiving sensitivity can be obtained also in a pipe axis direction, thereby a high detection capability can be obtained. Since the acoustical lens is used, the focal length can be easily changed only by replacing the lens, and setting can be easily adjusted when a pipe size is changed.

Figure 20:
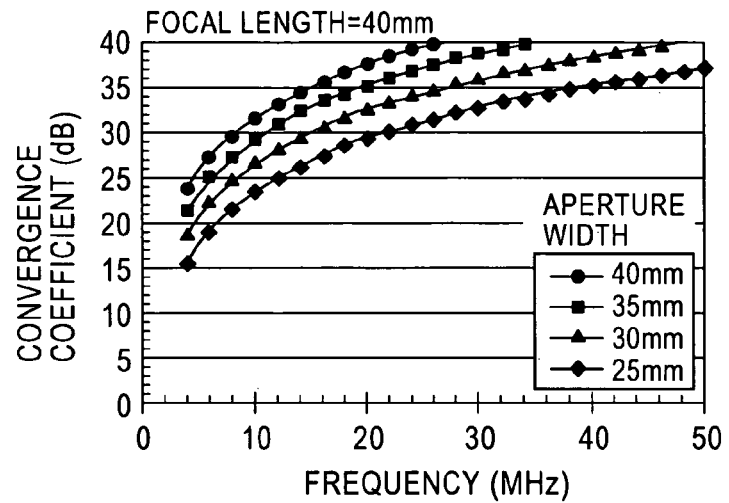
FIG. 20 is a view explaining a relationship between a frequency and a focusing coefficient.

FIG. 20 is a view showing the relationship between the frequency and the focusing coefficient. As shown in FIG. 20, a higher focusing coefficient is preferable because a higher frequency can be achieved thereby. However, when the frequency exceeds 20 MHz, since the intensity of the ultrasonic wave signal is greatly attenuated when it transmits in steel, an extremely high frequency is not preferable. On the other hand, an extremely low frequency is not preferable because the focusing coefficient is lowered thereby. In a frequency by which the focusing coefficient is set to 5 dB or more, the lower limit of the frequency is 5 MHz. As described above, the frequency is preferably set to 5 to 25 MHz and more preferable to 15 to 20 MHz.

[Countermeasure to Seam Offset]

In the testing of a pipe, since it is difficult to keep the positional relation of the array probe by causing it to follow a seam, slight seam offset is liable to occur, and when the seam offset occurs, the scanning line of a transmitting wave does not intersect the scanning line of a receiving wave on a welding line.

In contrast, in a welded portion of a pipe member formed at a normal position in design, since the group of transducer elements for transmission and the group of transducer elements for reception and/or the angle of refraction in transmission and the angle of refraction in reception are set such that a plurality of different positions, which are located above and below the welded portion (diameter direction of the pipe member) and on the left and right sides of the welded portion (peripheral direction of the pipe member), are used as the focusing positions of at least any one of transmitting beams and receiving beams under the condition that the focusing positions of the transmitting beams are in coincidence with the focusing positions of the receiving beams, even if a seam position is offset, a combination of any ones of scanning lines intersect on the welding line, thereby the echo from a flaw can be securely detected.

Note that the present invention does not limit a subject to be measured to a-penetrator and can be applied to various types of testing. Further, the present invention can be also applied to a mode in which minute oxides such as a plurality of penetrators and cold joint flaws dispersingly exist.

Embodiment 1

Embodiments of the present invention will be explained below referring to the figures. FIG. 1 is a view explaining a first embodiment of the present invention. In the figure, 1 denotes a steel pipe as a to-be-tested member, 2 denotes a welded portion, 3 denotes a flaw in a wall thickness inside portion, 4 denotes water for transmitting an ultrasonic wave, 5 denotes a linear array probe, 6 denotes a group of transducer elements for transmission, 7 denotes a group of transducer elements for reception, 8 denotes a transmitting beam, and 9 denotes a portion showing the ultrasonic wave traveling from a flaw to the group of transducer elements for receptions (hereinafter, also called a receiving beam), respectively. Further, the lines drawn between the transmitting beam 8 and the receiving beam 9 show scanning lines, respectively.

The linear array probe 5 has such a size that the ultrasonic wave, which is transmitted from the group of transducer elements located to a side near to the welded portion 2 (left side direction in FIG. 1), is directly incident thereon from the outside surface of a steel pipe of the welded portion and the ultrasonic wave, which is transmitted from the group of transducer elements located to a side far from the welded portion 2, is incident on the outside surface of the steel pipe of the welded portion after it is reflected once on the inside surface of the steel pipe. Then, the linear array probe 5 is disposed with an angle of incidence to the outer peripheral surface of the steel pipe so that a transmitting beam emitted from a center vertically enters from the outside surface side of the steel pipe as a transverse wave with an angle of refraction of 45° and is incident on the edge of the steel pipe of the welded portion on the inside surface side thereof (called 0.5 skips)

The ultrasonic wave beam from the group of transducer elements for transmission 6 is slightly deflected to the center axis side of the array probe according to the outside diameter of the steel pipe so that it has an angle of refraction of 45° as well as a delay time is set to the respective transducer elements so that the ultrasonic wave beam is focused at a position traversing the welded portion 2. Likewise, the group of transducer elements for receptions 7 is selected such that it can receive the echo reflected from the flaw 3 as an echo reflected once on the inside surface, the directionality thereof is slightly deflected to the center axis side of the array probe according to the outside diameter of the steel pipe so that it has an angle of refraction of 45° as well as a delay time is set to the respective transducer elements so that the ultrasonic wave beam is focused at a position traversing the welded portion 2. The angle of refraction is not limited to 45°, and the range of about 30° to 70°, at which testing can be carried out by the transverse wave, can be applied to it. However, the range of about 35° to 55°, at which the transverse wave totally reflected, is preferable in consideration of the angle dependency of the reflection coefficient of sound pressure when the transverse wave is reflected on a flaw and on the inside surface. Further, the range of 40° to 50° may be employed in view of stability.

As described above, the positions, the numbers, and the angles of refraction of the groups of transducer elements of the transmitting beam and the receiving beam are set such that they are focused according to the position of the welding unit, and the positional relation of the groups of transducer elements is set such that they can detect the echo from a flaw, thereby a minute flaw in the wall thickness inside portion can be detected.

Figure 2:
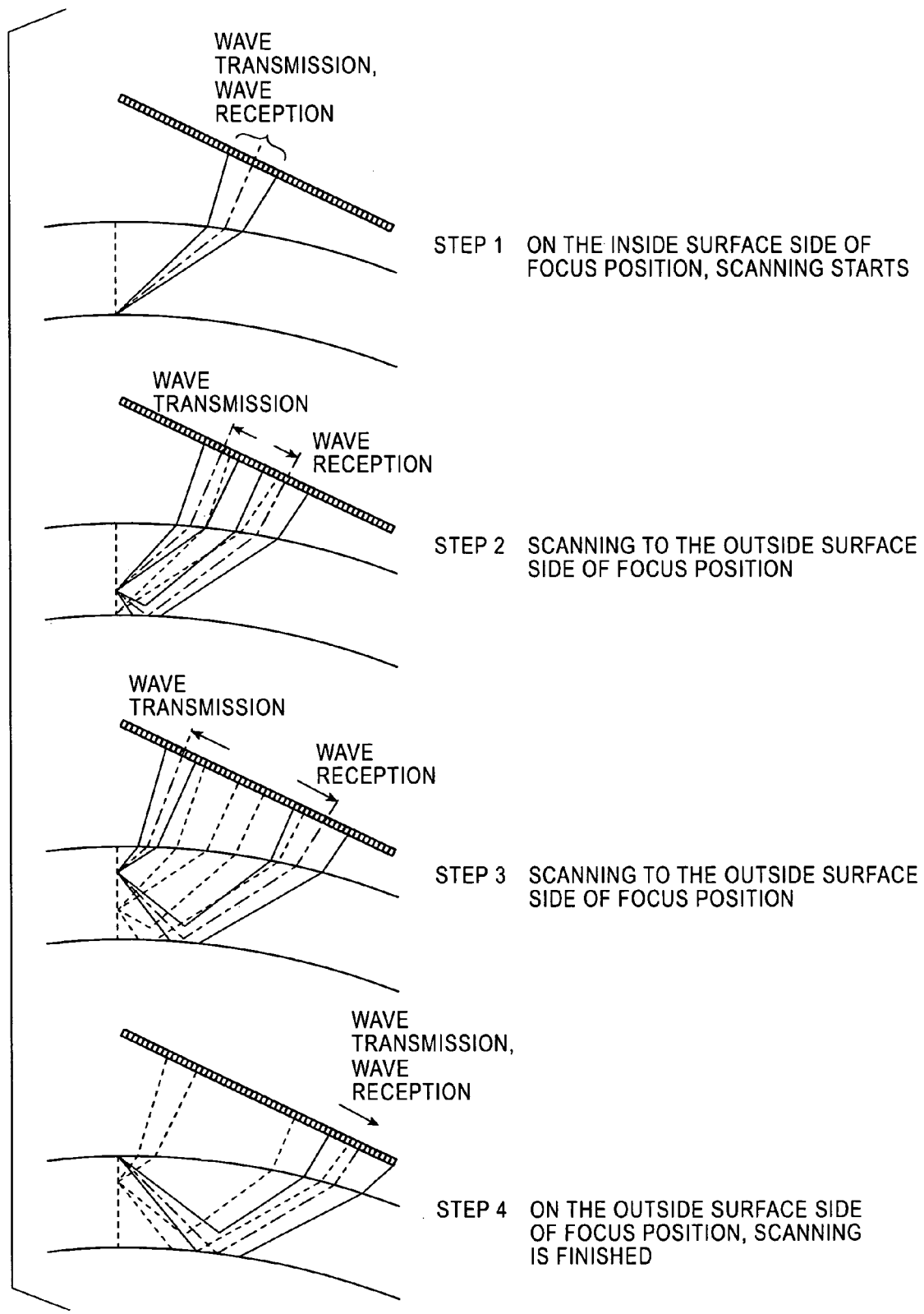
FIG. 2 is a view showing an example of a procedure of scan in the first embodiment of the present invention.

Next, FIG. 2 shows an example of a procedure for scanning the welded portion extending from the inside surface of the steel pipe to the outside surface thereof. First, at step 1 showing the start of scanning, testing is carried out to the focusing position (focus position) of the welded portion of the steel pipe on the inside surface side thereof by a 0.5 skip reflection technique using the group of transducer elements in the vicinity of the center of the linear array probe. At the time, a wave transmission and a wave reception are carried out by the same group of transducer elements. Next, at step 2, the group of transducer elements for transmission is offset to the welded portion side as well as the group of transducer elements reception is offset to a side far from the welded portion and a focus position is set to a position slightly above the welded portion on the inside surface side of the steel pipe (on the outside surface side of the steel pipe), thereby a wall thickness inside portion, which is located slightly above the welded portion on the inside surface side of the steel pipe, is tested by tandem testing. Continuously, at step 3, the group of transducer elements for transmission is offset to the welded portion side and the group of transducer elements for reception is offset to a side opposite to the welded portion, and testing is carried out by moving a test position in the welded portion to the outside surface side of the steel pipe. Although the figure shows only the steps 2 and 3, actually, the number of times at which the groups of transducer elements are offset is determined so that the ultrasonic wave beams partly overlap in order to carry out the testing effectively without omission (oversight) and overlap of the testing in consideration of the focus point size of the ultrasonic wave (beam size at a focus position). Finally, step 4 shows an end of scanning, and testing is carried out to the outside surface side of the welded portion using the group of transducer elements located on the side far from the welded portion by a 1.0 skip reflection technique. The testing can be carried out to the entire surface and the entire length of the welded portion (from the outside surface side of the steel pipe to the inside surface side thereof) by repeating steps 1 to 4 as well as mechanically scanning the relative positions between the steel pipe and the linear array probe in a pipe axis direction.

Figure 19:
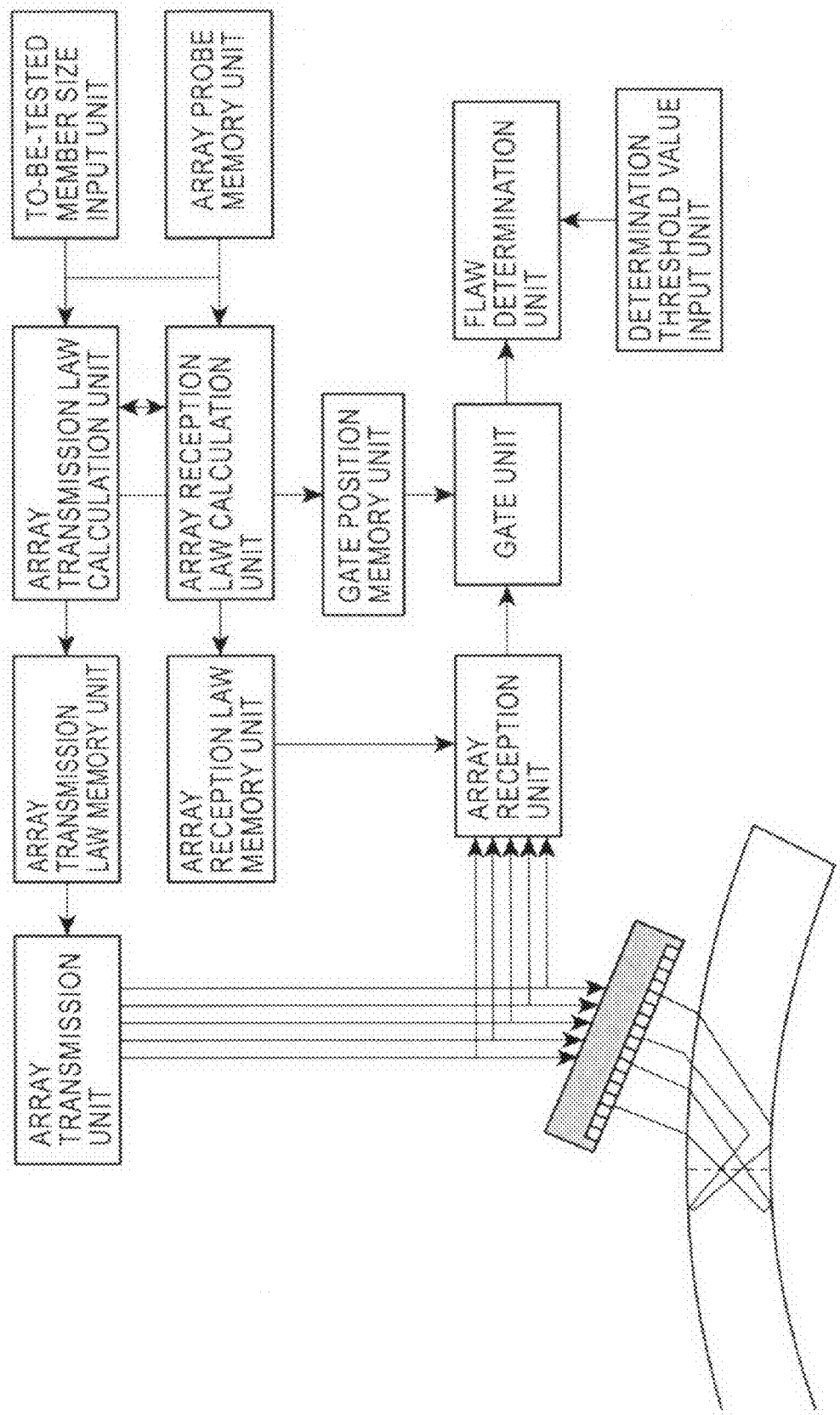
FIG. 19 is a view showing a functional arrangement example of an ultrasonic testing system according to the present invention.

FIG. 19 is a view showing an example of a functional arrangement of the ultrasonic testing system according to the present invention. The values of the outside diameter and the wall thickness of a steel pipe to be tested are input to a to-be-tested member size input unit from an operator or a process computer. An array probe memory unit stores the frequency of the array probe, the pitch of the transducer elements, and the number of the transducer elements.

An array transmission law calculation unit calculates the position of the transmission array probe, the number of transmission scanning lines, the transmission beam paths of respective scanning lines, the number of the transducer elements of the group of transducer elements for transmission of the respective scanning lines, the position of the group of transducer elements for transmission, focal lengths, and deflection angles according to the size of a steel pipe and to the specification of the array probe, and further calculates the delay times of the respective transducer elements of each scanning line. The respective values determined as described above are called an array transmission law.

Likewise the array transmission law calculation unit, an array reception law calculation unit calculates the position of the array probe, the number of reception scanning lines, the reception beam paths of the respective scanning lines, the number of the transducer elements of the group of transducer elements for reception of the respective scanning lines, the positions of the group of transducer elements for reception, focal lengths, and deflection angles are calculated according to the size of the steel pipe and to the specification of the array probe, and further the delay times of the respective transducer elements of each scanning line are calculated likewise the array transmission law calculation unit. The respective values determined as described above are called an array reception law.

Further, the positions of testing gates are determined based on the beam paths calculated by the array transmission law calculation unit and the array reception law calculation unit and stored to a gate position memory unit.

Note that, here, the array reception law may be determined based on the array transmission law determined previously, or the array reception law may be determined based on the array transmission law determined previously on the contrary. The array transmission law and the array reception law determined as described above are stored to an array transmission law memory unit and an array reception law memory unit, respectively, and used to a transmission/reception control described below. An array transmission unit selects a group of transducer elements for transmission based on the array transmission law stored to the array transmission law memory unit and generates transmission pulses by providing the respective elements with a delay time. An array reception unit selects a group of transducer elements for reception based on the array reception law stored to the array reception law memory unit, adds signals by providing the respective elements with a delay time, and obtains a testing waveform. A gate unit extracts the signal at a gate position stored to a gate unit memory unit.

A flaw determination unit compares a flaw determination threshold value input to a flaw determination threshold value input unit with the intensity of a signal in a gate, and when the intensity of the signal is equal or larger than the threshold value, it is determined that the signal shows a flaw. When testing carried out using one scanning line is finished as described above, a next group of transducer elements for transmission is selected based on the array transmission law stored to the array transmission law memory unit, and the testing is repeated thereafter likewise the above manner. Note that a flaw may be determined when the intensity of the signal is equal to or larger than the threshold value a plurality of time.

Figure 14:
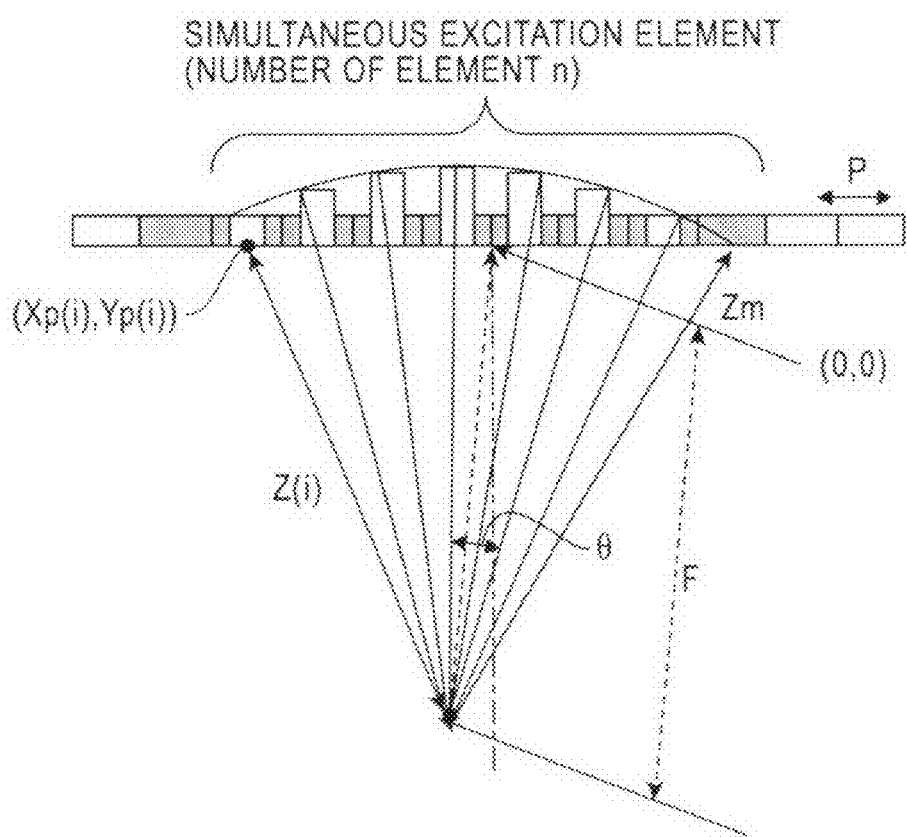
FIG. 14 is a view explaining a calculation of a delay time applied to respective transducer elements.

A procedure for controlling the groups of transducer elements to scan a beam in the thickness direction of the welded surface using the ultrasonic testing system will be explained. Specifically, it is sufficient to determine the groups of transducer elements for transmission and reception, the number of the transducer elements, the deflection angle, and the focal length by the following procedure. Here, the explanation will be carried out appropriately referring to FIG. 1 or FIG. 4 assuming that the widths of the groups of transducer elements used to transmission and reception are determined from a focusing coefficient for obtaining necessary sensitivity so that an angle of refraction is made to a predetermined angle. Note that since the contents of a), b), g) shown below correspond to 1), 2), 3) described above, they will be concisely explained here.

a) The position of the linear array probe is determined such that the beam, which is transmitted vertically from the transducer element located at the center of the linear array probe to the prove surface thereof, enters a steel pipe as a transverse wave having a predetermined angle of refraction (for example, an angle of refraction of 45°) and is incident on the welded portion on the inside surface side of the steel pipe or the welded portion on the outside surface side of the steel pipe.

b) Points of incidence are geometrically determined such that the angles of incidence from the respective transducer elements to the outside surface of the steel pipe are set to predetermined angles at all times or within a predetermined range, and further lines (scanning lines) passing in the steel pipe at an angle of refraction of 45° are determined. The respective transducer elements referred to here are the transducer elements corresponding to the center position of the transmitting unit, thereby the positional relationship between the group of transducer elements of the transmitting unit and the points of incidence of the outside surface of the steel pipe is determined. Further, the transmission paths of the beams after they are incident on the steel pipe, that is, the points of reflection on the inside surface, the points of reflection on the outside surface, and the points of reflection on the welded surface are determined corresponding to the angle of refraction.

c) The deflection angles of the respective scanning lines are calculated from the positional relations between the points of incidence and the transducer elements.

d) The water paths (lengths) of the respective scanning lines and the path lengths in steel up to the welded portion are calculated and a focal length F in water is determined by converting them in steel by a sound speed and the water path.

e) The apertures D of the respective scanning lines are calculated from the equation (2), and the number n of the transducer elements of the groups of transducer elements of the respective scanning lines is determined by dividing the apertures D by the pitch of the transducer elements and rounding off a resultant quotient. A reason why the apertures D are determined from the equation (2) is to satisfy the value of the focusing coefficient necessary to secure sensitivity.

f) The positions of the respective groups of transducer elements constituting the transmitting unit are determined from the positions and the number n of the transducer elements of the respective scanning lines.

g) The scanning lines used for testing are determined as well as a group of transducer elements for transmission paired with a group of transducer elements for reception is determined from the positional relation of the respective scanning lines intersecting the welded portion. It is sufficient to select a pair of scanning lines transmitting from opposite directions and intersecting on the welded portion as a pair of the transmitting unit and the receiving unit. Further, when scanning lines are overlapped more than necessary to a space resolution to which the same location of the welded portion is required, they may be thinned out.

h) Since the number of the groups of transducer elements, the focal lengths, and the deflection angles are determined as to all the scanning lines used to testing, the delay times applied to the transducer elements are calculated, respectively. The known technique disclosed in Patent Document 5 filed by the inventors previously may be used as a technique for calculating the delay times. A basic concept of the calculation will be explained below referring to FIG. 14 and equations. First, when the center position of the group of transducer elements is used as the origin of a coordinate, a focal length is shown by F, and a deflection angle is shown by θ, the coordinate {Xf, Yf} of a focus position is determined as follows.

$Xf = F \cdot \sin\theta, Yf = -F \cdot \cos\theta$

Next, when a pitch of the transducer elements is shown by P, the number of the transducer elements of the group of transducer elements is shown by n (however, n is an odd number), the coordinate {Xp(i), Yp(i)} of the respective transducer elements is determined as follows.

$Xp(i) = -n \cdot p/2 - p/2 + p \cdot i, Ypi = 0 (i=1 \text{ to } n)$

Further, the distance Z(i) between the focus position and the respective transducer elements and the maximum value Zm of the distance are determined as follows.

$Z(i) = SQRT\{(Xf-Xp(i))2+(Yf-Yp(i))2\} (i=1 \text{ to } n)$ $Zm = \max\{Z(i)\} (i=1 \text{ to } n)$ Finally, the delay time Δt(i) is determined by the following equation. Note that C shows a sound speed.

$\Delta t(i) = (Zm - Z(i))/C (i=1 \text{ to } n)$

Note that although the basic concept of the calculation is shown above, it is not always necessary to set the center position of the group of transducer elements as the origin of the coordinate as to each of the respective scanning lines. Further, although the number n of the transducer elements is the even number in the above explanation, it may be an odd number. When it is the odd number, it is needless to say that the above equations can be applied by being partly modified. In an actual calculation, it is sufficient to previously determine the respective coordinates of the array probes, to determine the coordinate of the focus position according to the focal length and the deflection angle, and to determine the distances Z(i) between the focus position and the transducer elements.

Figure 4:
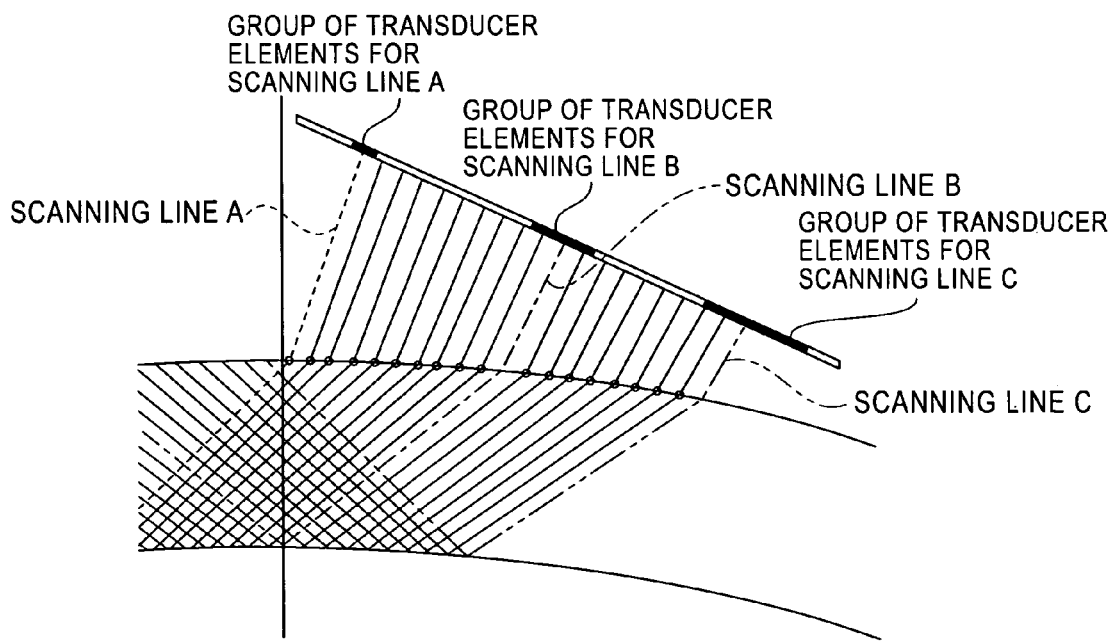
FIG. 4 is a view showing scanning lines and an example of a result of calculation of test conditions of typical points.

FIG. 4 is a view showing an example of scanning lines determined as described above and a result of calculation of a test condition of the typical points of the scanning lines. FIG. 4 shows an example when a steel pipe having an outside diameter of ϕ558.8 mm and a wall thickness of 25.4 mm was tested by a linear array probe having 160 elements (transducer elements) having intervals set to a pitch of 0.5 mm at an ultrasonic wave frequency of 15 MHz with a water path of 20 mm at a center at an angle of refraction of 45°. Here, the number of the transducer elements is set to 1 on a side near to the welded portion and to 160 on a side far from the welded portion.

Since the focal lengths at the positions of the respective transducer elements are determined as shown in a table of FIG. 4, the curvature of an acoustical lens for focusing the ultrasonic wave in a pipe axis direction is also determined based on the focal lengths. As known well, the curvature r of the acoustical lenses is determined by an equation (3), where C1 shows the sound speed of a material of the acoustical lenses, and C2 shows the sound speed of water, and F shows a focal length in water, respectively.

$$r = \left(1 - \frac{C2}{C1}\right) \cdot F \quad (3)$$

Note that a scanning line A is shown by a double-dashed line, a scanning line B is shown by a broken line, and a scanning line C is shown by a single-dashed line, and both the sides of the scanning lines A, B, C are shown by white color to make the figure understandable. Further, the black portions of the probe show the groups of transducer elements for transmitting and receiving the respective scanning lines.

Figure 5:
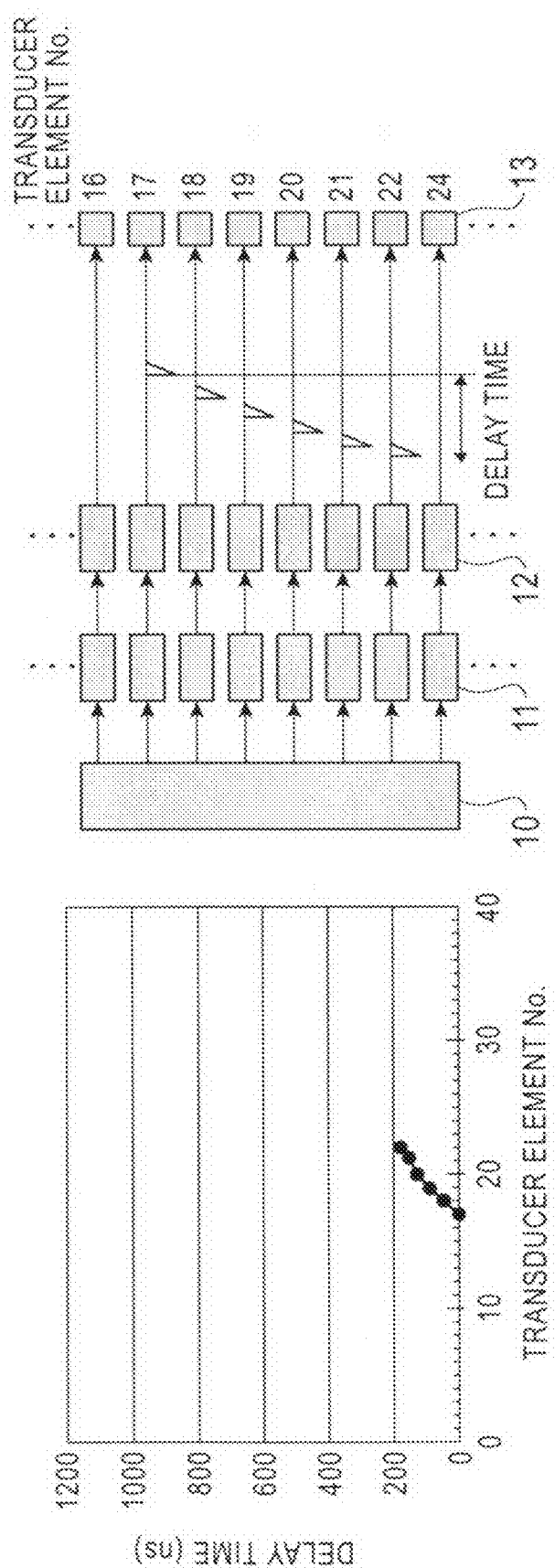
FIG. 5 is a view showing a result of calculation of a delay time of a scanning line A and a principle of wave transmission.

FIG. 5 is a view showing a result of calculation of a delay time calculated as to the scanning line A shown in FIG. 4 and a principle of transmission. In the figure, 10 denotes a test condition calculation unit for calculating the above items 1) to 8), 11 denotes a delay time setting unit for determining the transmission timing of a transmitting pulse based on the calculation, 12 denotes a pulser, and 13 denotes the respective transducer elements of the linear array probe. The figure shows that only the transducer elements Nos. 17 to 22 are selected, the transducer element having the number 17 is excited first, and then the transducer elements up to Nos. 18 to 22 are gradually excited with a time delay. A transmitting beam corresponding to the scanning line A is created by the above operation.

Figure 6:
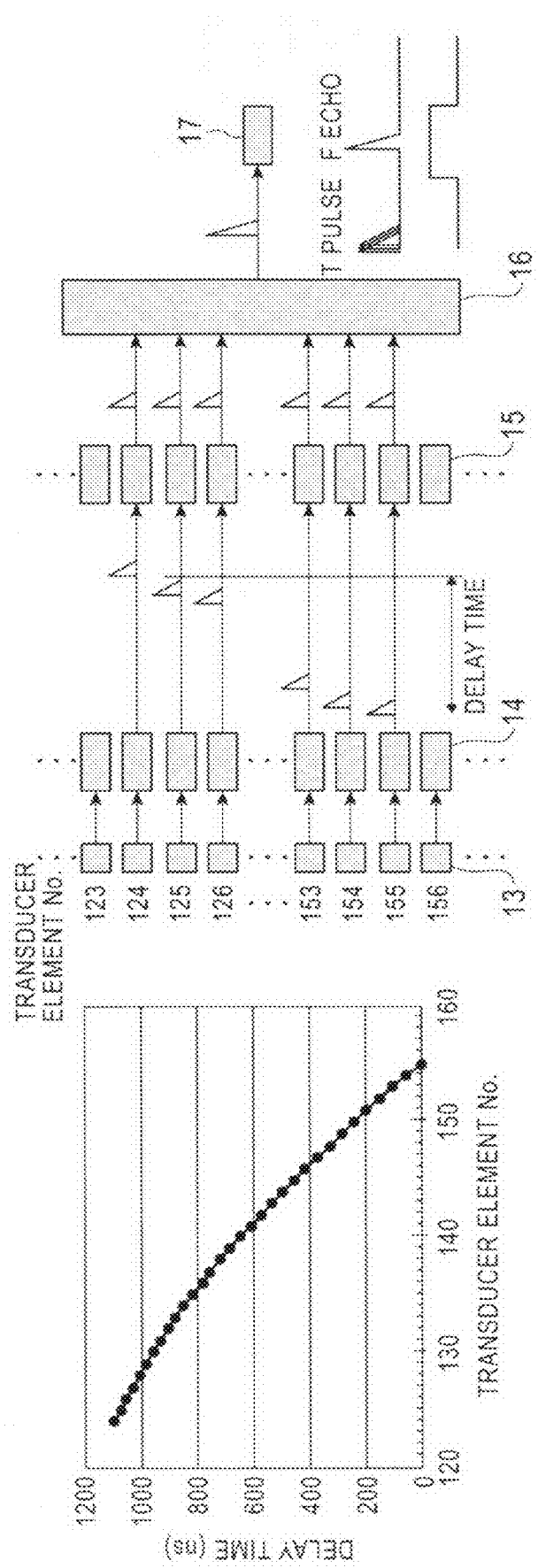
FIG. 6 is a view showing a result of calculation of a delay time of a scanning line C and a principle of wave reception.

FIG. 6 is a view showing a result of calculation of a delay time calculated as to the scanning line C shown in FIG. 4 and a principle of reception. In the figure, 13 denotes the respective transducer elements of a linear array probe, 14 denotes a receiving amplifier, 15 denotes a delay time setting unit, 16 denotes a synthesization processing unit, and 17 denotes a gate evaluation unit. The figure shows that only the transducer elements having the numbers 124-155 are selected, the echo from a flaw is incident on the transducer element having the number of 124 first, the transducer elements up to Nos. 125 to 155 are gradually received with a time delay, the time delays are corrected by the delay time setting unit 15 so that phases agree with each other, the phases are synthesized by the synthesization processing unit 16, and the echo is increased by a focusing effect.

With this operation, wave reception corresponding to the scanning line C is carried out. Thereafter, the gate evaluation unit 17 determines whether or not a flaw echo (F echo in the figure) exits in a time region (gate) set to a distance according to a beam length from a transmitting pulse (T pulse in the figure), and testing is carried out. Note that the operations carried out by the delay time setting unit 15, the synthesization processing unit 16, and the gate evaluation unit 17 can be also carried out by processing a signal by software after the signal is output from the receiving amplifier 14, is subjected to A/D conversion at once, and stored to a memory.

Figure 7:
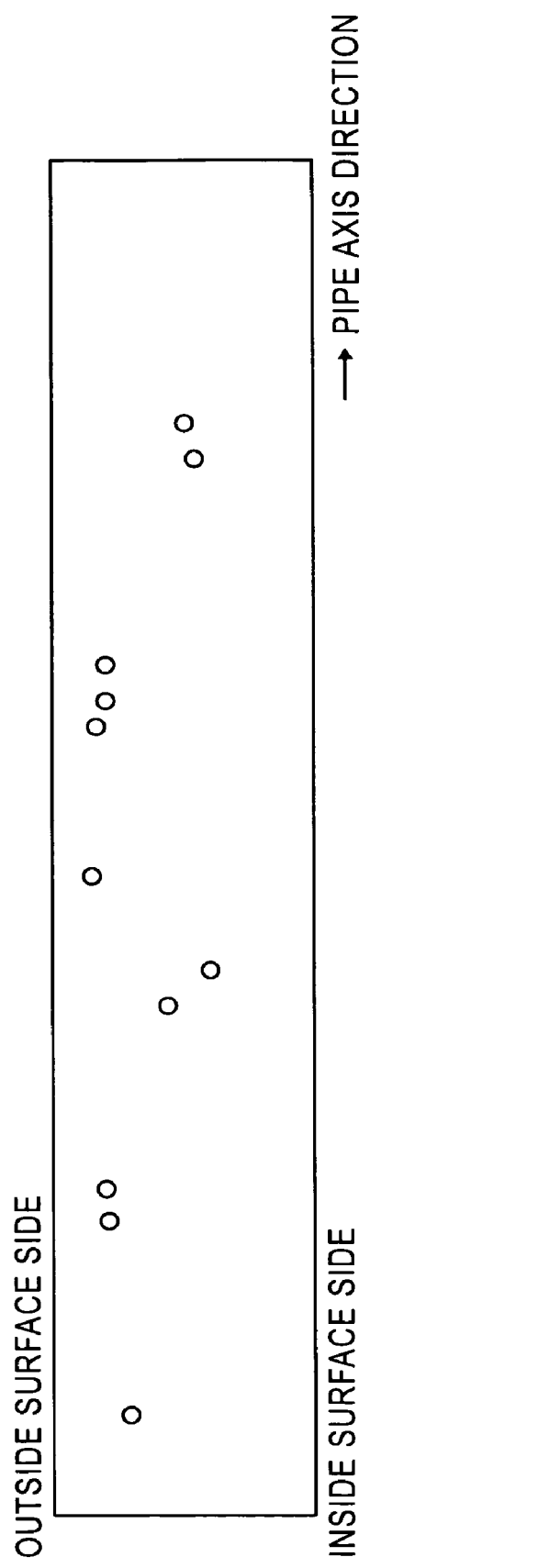
FIG. 7 is a view showing a result of test of a welded portion (an example of a minute flaw distribution).

FIG. 7 is a view showing a result (an example of distribution of a minute flaw) that a welded portion is tested while it is mechanically scanned in a pipe axis direction using a linear array probe whose transducer elements has a width set to 10 mm in the pipe axis direction and an acoustical lens and using the value determined as described above. A minute flaw of several hundreds of micron meters whose detection by the conventional angle beam testing technique is difficult can be detected together with a wall thickness central portion.

In the embodiment, the test condition is calculated sequentially after the points of incidence of the respective scanning lines are determined first as shown in the items 2) and the subsequent items. However, the present invention is not limited thereto, and, for example, the test condition may be determined by determining a focus position and then determining the paths having a shortest transmission time to the focus position by search as to the respective transducer elements.

Embodiment 2

Figure 8:
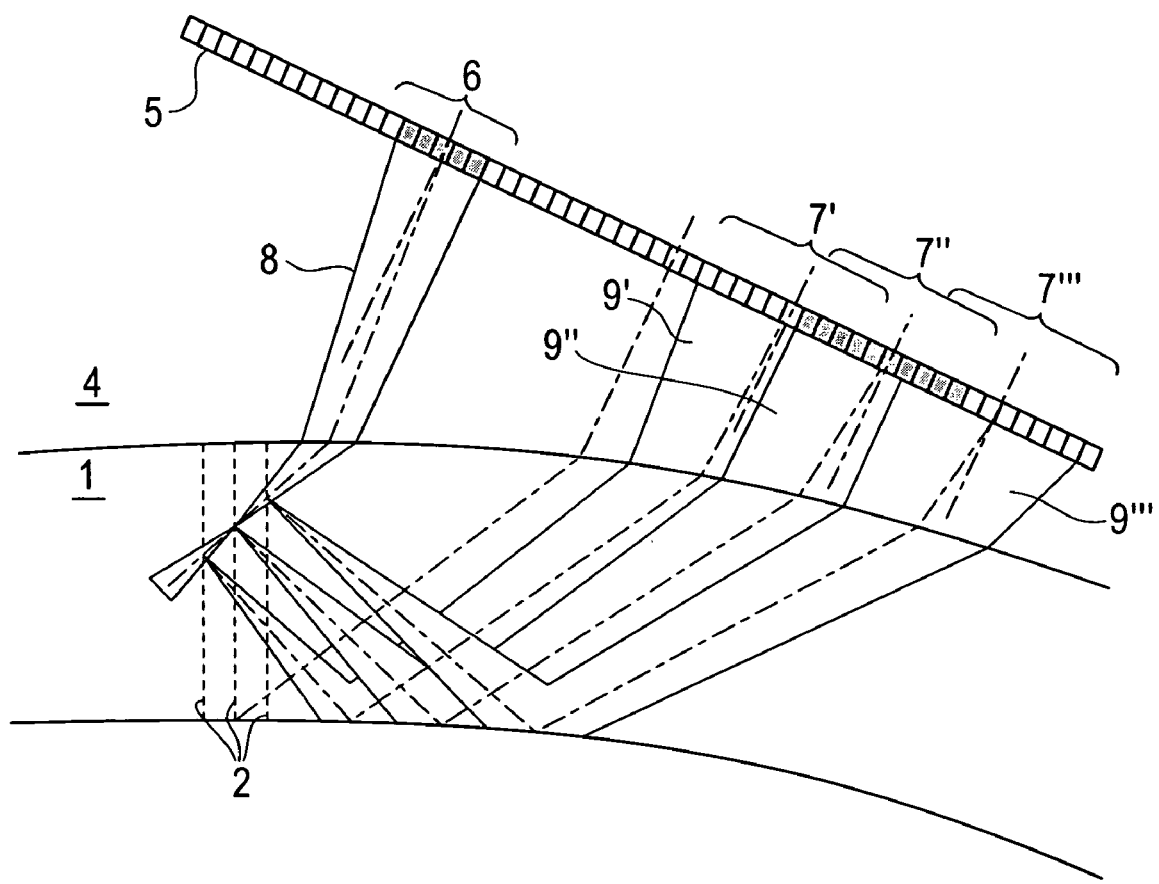
FIG. 8 is a view explaining a second embodiment of the present invention.

Next, a second embodiment of the present invention will be explained. FIG. 8 is a view explaining the second embodiment of the present invention and shows setting and a procedure of testing at step 3 shown in FIG. 2. In the figure, 7' to 7''' show groups of transducer elements for reception, and 9' to 9''' show receiving beams. In the embodiment, a transmitting beam 6 is transmitted from a group of transducer elements for transmission 5 and received by the group of transducer elements for reception 7' first. Next, the transmitting beam 6 is transmitted from the group of transducer elements for transmission 5 and received by the group of transducer elements for receptions 7''. Finally, the beam 6 is transmitted from the group of transducer elements for transmission 5 and received by the group of transducer elements for receptions 7'''. With this operation, even if the position of a welded portion is swung right and left as shown in the figure because the position of a welded point cannot be specified, a positioning accuracy is bad, vibration occurs, and the like, since scanning lines intersect the welded portion by any of combinations thereof, a flaw can be detected without omission.

Embodiment 3

Figure 9:
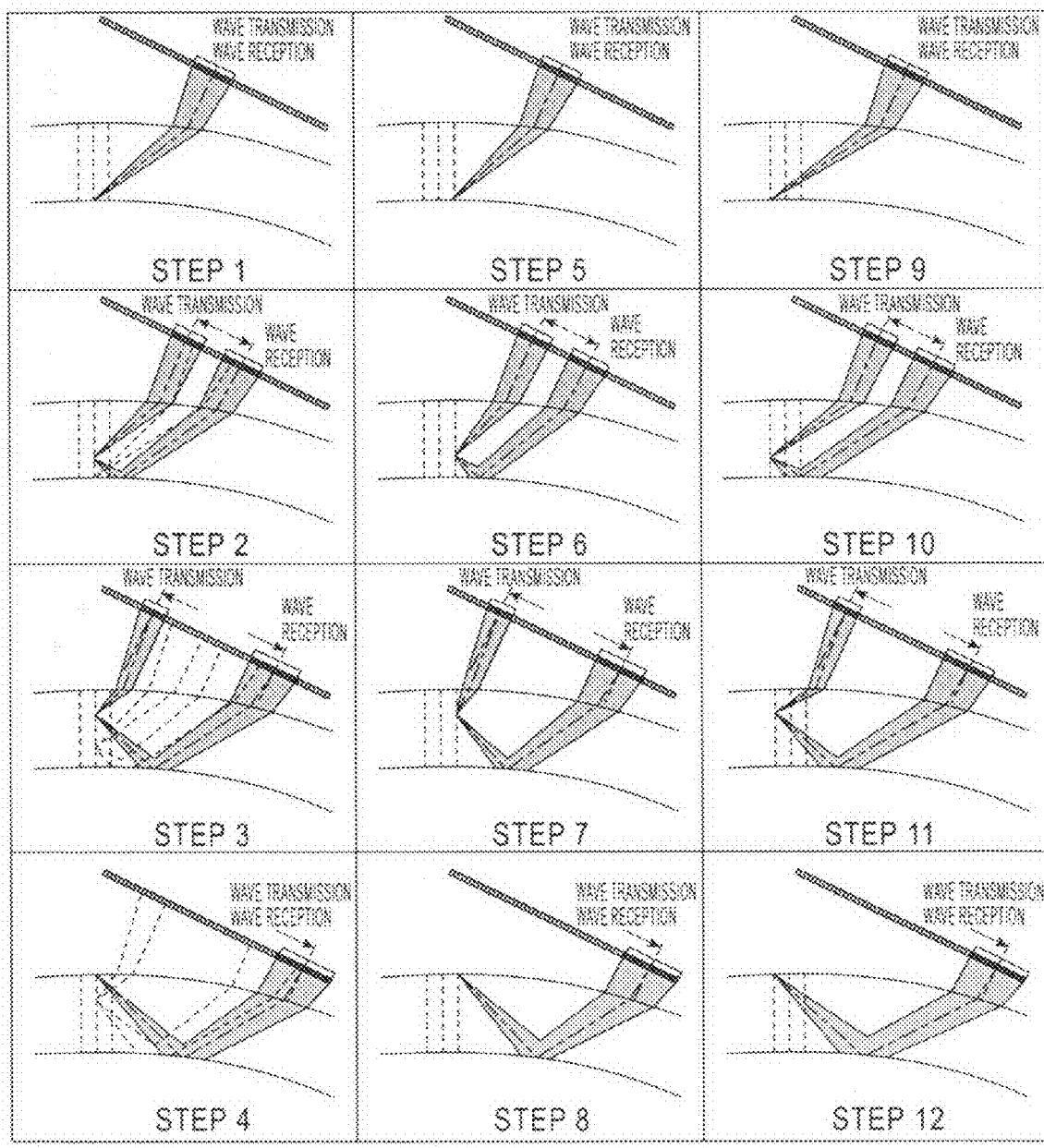
FIG. 9 is a view explaining a third embodiment of the present invention.

Next, a third embodiment of the present invention will be explained. FIG. 9 is a view explaining the third embodiment of the present invention. In the third embodiment, after the entire wall thickness of a certain portion in a pipe peripheral direction is tested at steps 1 to 4 of FIG. 2, the proximal side (right side in the figure) of the scanning position is tested at next steps 5 to 8 and further the distal side thereof (left side in the figure) is tested at steps 9 to 12.

With this operation, even if a flaw is swung right and left because the position of a welded point cannot be specified, a positioning accuracy is bad, vibration occurs, and the like, since scanning lines intersect a welding line by any of the combinations thereof, the flaw can be detected without omission. Although three scanning lines intersect an intersecting position in FIG. 3, the present invention is not limited thereto. The intersecting position of scanning lines can be offset by a technique offsetting the position of a group of transducer elements for transmission or reception, changing a deflection angle, and the like.

Embodiment 4

Figure 10:
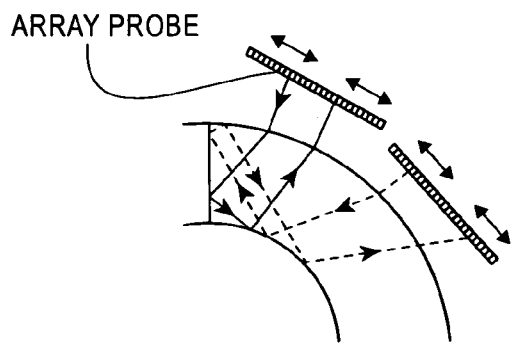
FIG. 10 is a view explaining a fourth embodiment of the present invention.

Next, a fourth embodiment of the present invention will be explained. In the first embodiment, the entire area in a welded surface thickness direction (pipe diameter direction) is scanned by the one array probe. However, in the fourth embodiment, a plurality of array probes each having a transmitting unit and a receiving unit disposed therein are disposed in a peripheral direction (pipe diameter direction), a steel pipe is divided in the welded surface thickness direction and each divided portion is scanned by each array probe as shown in FIG. 10.

In the example, two array probes are used, testing is carried out from an inside surface to a wall thickness center portion using the array probe on the left side in the figure, and further testing is carried out from the wall thickness center portion to an outside surface using the array probe on the right side. When it is intended to test from the inside surface to the outside surface using one array probe as shown in FIG. 2, the length of the array probe is increased particularly in a member having a large wall thickness. Thus, when a group of transducer elements for transmission or reception moves to the edge of the array probe, a deflection angle is increased, from which a problem arises in that sensitivity is deteriorated.

In contrast, in the embodiment, since the steel pipe is divided in the wall thickness direction and the divided portions are covered using the plurality of array probes, the length of the array probe is not increased, and a deflection angle is not too increased, thereby the deterioration of the sensitivity can be suppressed. When, for example, a steel pipe having a thickness of 25 mm at 22" by the first embodiment, a length of 88 mm is necessary to an array probe, and when a group of transducer elements is located nearest to an edge, a deflection angle is set to about ±5.9°.

When, for example, the width of one element of an array probe is set to 0.95 mm, and a frequency is set to 10 MHz, sensitivity is lowered by 17.4 dB by deflection. Even if it is intended to compensate the sensitivity by increasing a receiving gain, an S/N cannot be increased because electric noise is increased at the same time. On the other hand, in the embodiment, a length of only 60 mm is necessary to the array probe, and when the group of transducer elements is located to a distal edge, the deflection angle is set to ±3.4°, thereby sensitivity is lowered only by 5 dB. In this case, even if sensitivity is corrected by increasing the receiving gain, the electric noise is increased only a little.

Embodiment 5

Figure 11:
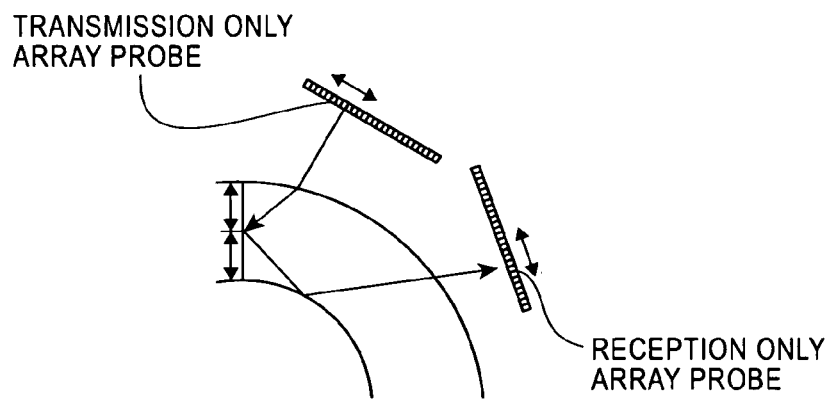
FIG. 11 is a view explaining a fifth embodiment of the present invention.

Next, a fifth embodiment of the present invention will be explained. In the first and fourth embodiments, the transmitting unit and the receiving unit are disposed in one array probe. However, in the fifth embodiment, an array probe used only for transmission and an array probe used only for reception are separately provided, and a plurality of array probes is disposed as shown in FIG. 11. With this arrangement, since the optimized array probes can be used to transmission and reception, sensitivity can be improved. Further, since an optimum angle can be set to respective steel pipes, a deflection angle is reduced and deterioration of sensitivity can be suppressed.

Embodiment 6

Figure 12:
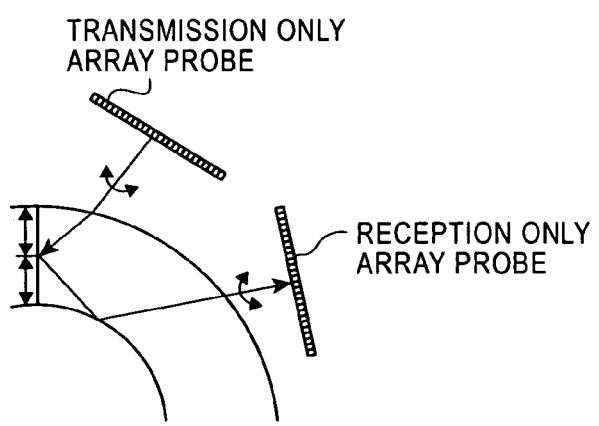
FIG. 12 is a view explaining a sixth embodiment of the present invention.

Up to the fifth embodiment, the transmitting unit and the receiving unit are arranged using a part of the groups of transducer elements of the array probes, and the welded surface is manipulated while the transmitting and receiving units are moved. However, in a sixth embodiment, an array probe for transmission and an array probe for reception are provided separately, a plurality of array probes are disposed, and transmission and reception are carried out by all the groups of transducer elements of the array probes as shown in FIG. 12. As a technique for scanning the welded surface, a deflection angle is changed to set the intersecting position of a transmitting beam and a receiving beam. With this operation, since all the elements the array probes can be used as the groups of transducer elements, an aperture is increased, thereby a focusing coefficient can be increased. When the positions of the array probes are fixed here, since a transmitting beam and a receiving beam are not placed in the relationship of mirror reflection with respect to a welding line, the deflection angle may be changed as well as the positions of the transmission array probes or the reception array probes may be mechanically moved so that the transmitting beam and the receiving beam is placed in the relationship of mirror reflection on a welding line.

Embodiment 7

Figure 13:
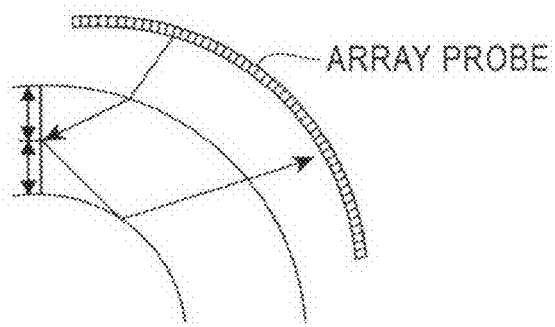
FIG. 13 is a view explaining a seventh embodiment the present invention.

Next, a seventh embodiment of the present invention will be explained. In the seventh embodiment, an array probe is formed in conformity with a curvature of a pipe as shown in FIG. 13. With this arrangement, even if a position of incidence of transmission and reception is changed, scanning can be easily carried out in a state that a deflection angle and an angle of refraction are kept to predetermined angles without the need of carrying out complex arithmetic processing as in the linear array probe, thereby the dispersion of sensitivity can be suppressed different from the embodiments 1 to 6.

Note that the arrangements of the embodiments 4 to 7 are not limited to the arrangements used independently and may be appropriately combined. For example, a welded surface may be divided into an inside surface and an outside surface, the inside surface side may be arranged according to the embodiment 4, the outside surface may be arranged according to the embodiment 5, and the embodiments 4 and 5 may be combined, or an array probe having a curvature of a pipe as in the embodiment 7 may be combined with the control of an angle of refraction and a delay time.

INDUSTRIAL APPLICABILITY

According to the present invention, since minute flaws of several hundreds of micron meters or less located in the wall thickness inside portion of a welded portion of a seam-welded pipe and the like can be detected from an outside surface to an inside surface without omission, a welding process can be improved such that no minute flaw, which influences the mechanical characteristics of a welded portion of a welded steel pipe, does not occur or flaws can be screened in a manufacturing process to prevent them from still remaining. As a result, the quality of a welded steel pipe can be outstandingly improved or the welded steel pipe can be used under the conditions more sever than ever.

The invention claimed is:

1. An ultrasonic testing system for a pipe member, comprising:
a transmitting/receiving unit including a transmitting unit, which transmits an ultrasonic wave to a welded surface of a welded portion in a pipe axis direction of a pipe member and to an inside surface of the pipe member so that the ultrasonic wave is incident at an angle within a range from 33.2° to 56.8°, and a receiving unit, which partly or entirely receives an echo reflected in a direction within a range from −12° to 16° to a mirror reflecting direction in the welded surface, wherein the transmitting unit and the receiving unit are composed of different groups of transducer elements on at least one array probe disposed in a pipe member peripheral direction; and
a controller for scanning the pipe member in a thickness direction by carrying out control to change the groups of transducer elements corresponding to the transmitting unit and the receiving unit on said at least one array probe or to change an angle of said at least one array probe, and controlling the angle of incidence of the ultrasonic wave to the pipe member in the respective transmitted wave and received wave so that the angles of incidence to the welded surface and the inside surface and the angle of the echo on the welded surface are kept within the ranges defined as to the transmitted wave and the received wave, respectively.

2. An ultrasonic testing system for a pipe member according to claim 1, wherein the controller controls the angle of incidence and a focus position of the ultrasonic wave to the pipe member by offsetting at least one of a timing of wave transmission and a timing of wave reception of the respective transducer elements in the groups of transducer elements so that the angles of incidence to the welded surface and the inside surface and the angle of the echo on the welded surface are kept within the ranges defined as to the transmitted wave and the received wave, respectively.

3. An ultrasonic testing system for a pipe member according to claim 1, wherein the angle of incidence of at least one of the ultrasonic wave on a transmitting side and the ultrasonic wave on a receiving side to the pipe member is kept to a predetermined angle.

4. An ultrasonic testing system for a pipe member according to claim 3, wherein the controller controls at least one of the wave transmitted from and the wave received by the respective transducer elements so that the angle of incidence of the ultrasonic wave to the pipe member is made to be a predetermined angle.

5. An ultrasonic testing system for a pipe member according to claim 4, wherein the controller controls the angle of incidence and a focus position of the ultrasonic wave to the pipe member by offsetting at least one of a timing of wave transmission and a timing of wave reception of the respective transducer elements in the groups of transducer elements based on a curvature of the pipe member.

6. An ultrasonic testing system for a pipe member according to claim 3, wherein said at least one array probe provides the groups of transducer elements with a curvature so that they are disposed along the peripheral direction of the pipe member.

7. An ultrasonic testing system for a pipe member according to claim 1, wherein at least one of the transmitting unit and the receiving unit transmits or receives an ultrasonic wave having a focusing coefficient in a range of 5 dB to 50 dB.

8. An ultrasonic testing system for a pipe member according to claim 1, wherein said at least one array probe includes an acoustical lens for focusing the transmitted wave and received wave in the pipe axis direction of the pipe member, and a focal length of the acoustical lens is set shorter as it is nearer to the welded portion and longer as it is farther from the welded portion.

9. An ultrasonic testing system for a pipe member according to claim 1, wherein the transmitting/receiving unit comprises a plurality of array probes and includes a transmitting unit and a receiving unit on each array probe.

10. An ultrasonic testing system for a pipe member according to claim 1, wherein the transmitting unit and the receiving unit of the transmitting/receiving unit comprise different array probes.

11. An ultrasonic testing system for a pipe member according to claim 1, wherein:
the transmitting unit and the receiving unit of the transmitting/receiving unit comprise different array probes; and
the controller changes deflection angles of the transmitted wave and the received wave from the respective array probes.

12. An ultrasonic testing system for a pipe member according to claim 1, wherein the controller changes the angle of incidence and a focus position of the ultrasonic wave to the pipe member in at least one of the transmitted wave and the received wave so that scanning lines of the transmitted wave intersect scanning lines of the received wave at a plurality of positions.

13. An ultrasonic testing method for a pipe member, wherein the ultrasonic testing method uses an ultrasonic testing system for a pipe member comprising a transmitting unit and a receiving unit composed of different groups of transducer elements on at least one array probe disposed in a pipe member peripheral direction, the method comprising:
transmitting an ultrasonic wave to a welded surface of a welded portion in a pipe axis direction of the pipe member and to an inside surface of the pipe member by the transmitting unit so that the ultrasonic wave is incident at an angle within a range from 33.2° to 56.8°;
partly or entirely receiving an echo reflected in a direction within a range from −12° to 16° to a mirror reflecting direction in the welded surface; and
scanning the pipe member in a thickness direction by carrying out control to change the groups of transducer elements corresponding to the transmitting unit and the receiving unit on said at least one array probe or to change an angle of said at least one array probe, while keeping the angles of incidence from the transmitting unit to the welded surface and the inside surface and the angle of the echo received by the receiving unit on the welded surface within the ranges defined as to the transmitted wave and the received wave, respectively.

14. An ultrasonic testing method for a pipe member according to claim 13, further comprising controlling the angle of incidence and a focus position of the ultrasonic wave to the pipe member by offsetting at least one of a timing of wave transmission and a timing of wave reception of the respective transducer elements in the groups of transducer elements.

15. An ultrasonic testing method for a pipe member according to claim 13, further comprising keeping the angle of incidence of at least one of the ultrasonic wave on a transmitting side and the ultrasonic wave on a receiving side to the pipe member to a predetermined angle.

16. An ultrasonic testing method for a pipe member according to claim 13, wherein at least one of the transmitting unit and the receiving unit transmits or receives an ultrasonic wave having a focusing coefficient in a range of 5 dB to 50 db.

* * * * *